US011574319B2

(12) United States Patent
Blackburn et al.

(10) Patent No.: US 11,574,319 B2
(45) Date of Patent: *Feb. 7, 2023

(54) SYSTEM FOR VERIFICATION AND MANAGEMENT FOR NON-FUNGIBLE TOKENS

(71) Applicant: Scientia Potentia Est., LLC, Charleston, SC (US)

(72) Inventors: Jeremy Blackburn, Charleston, SC (US); Justin Southward, Lehigh Acres, FL (US); W. Kurt Taylor, N. Charleston, SC (US); Karl David, Charleston, SC (US); Austi Critchfield, Clearwater, FL (US); Michael Lu, N. Charleston, SC (US); Tim McVicker, Charleston, SC (US)

(73) Assignee: Scientia Potentia Est II, LLC, Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/561,827

(22) Filed: Dec. 24, 2021

(65) Prior Publication Data

US 2022/0114600 A1 Apr. 14, 2022

Related U.S. Application Data

(63) Continuation-in-part of application No. 17/531,746, filed on Nov. 20, 2021, which is a (Continued)

(51) Int. Cl.

*G06Q 30/018* (2023.01)
*G06Q 20/40* (2012.01)

(Continued)

(52) U.S. Cl.

CPC ..... *G06Q 30/0185* (2013.01); *G06Q 20/1235* (2013.01); *G06Q 20/4015* (2020.05); *G06Q 20/40145* (2013.01)

(58) Field of Classification Search

CPC .......... G06Q 30/0185; G06Q 20/1235; G06Q 20/40145; G06Q 20/4015; G06Q 40/08;

(Continued)

(56) References Cited

U.S. PATENT DOCUMENTS 10,338,913 B2 * 7/2019 Franchitti .......... G06F 16/9538
2017/0031676 A1 * 2/2017 Cecchetti ............... G06F 21/64

* cited by examiner

*Primary Examiner* — Garcia Ade

(74) *Attorney, Agent, or Firm* — Kim and Lahey Law Firm, LLC; Douglas W. Kim

(57) ABSTRACT

A computerized system for verification and management of a digital asset, including an immutable digital asset, comprising: a computer system a sensor and a set of non-transitory computer readable instructions that can include instructions adapted for: receiving a digital asset from a creator of the digital asset; receiving significant information wherein the significant information is taken from a group consisting of date, time, event, individual, team, organization, notation, and any combination thereof; receiving identification information using the sensor of the creator; retrieving location information representing a physical location where the identification information is received, and the computer system is located; retrieving date and time information from the computer system; creating a digital asset record that includes a unique identifier associated with the digital asset, identification information, location information, and date and time information; and storing the digital asset record on the persistent storage.

30 Claims, 26 Drawing Sheets

102 104 112 106A 110A 108A 103 100 104 102 112 106B 110B 108B 100 103

Related U.S. Application Data continuation-in-part of application No. 17/531,598, filed on Nov. 19, 2021, which is a continuation-in-part of application No. 17/344,043, filed on Jun. 10, 2021, which is a continuation-in-part of application No. 17/176,056, filed on Feb. 15, 2021, now Pat. No. 11,288,308, which is a continuation-in-part of application No. 17/128,084, filed on Dec. 19, 2020, which is a continuation-in-part of application No. 16/997,840, filed on Aug. 19, 2020, which is a continuation-in-part of application No. 16/994,585, filed on Aug. 15, 2020, now Pat. No. 11,232,652, which is a continuation-in-part of application No. 16/991,916, filed on Aug. 12, 2020, now Pat. No. 11,216,823, which is a continuation-in-part of application No. 16/876,080, filed on May 17, 2020, which is a continuation-in-part of application No. 16/810,782, filed on Mar. 5, 2020, now Pat. No. 11,216,781.

(51) Int. Cl.
*G06Q 20/12* (2012.01)
*G06F 16/9538* (2019.01)

(58) Field of Classification Search
CPC ........ G16H 20/10; G16H 40/20; G16H 40/63; G16H 40/67
USPC .............................................................. 705/2
See application file for complete search history.

Biometric Data
602
Facial Image
603
Iris/Retinal Scan
604
Fingerprint Scan
606
Heart Rate Signature
614
Hand Scan
608
Voice Print
610
Other
612
600

Trigger Event
702
700
Trigger Alarm
704
Send Notification To Supervisor
706
Contract Authority
708
Prompt Individual to Prove Identity
710

SYSTEM FOR VERIFICATION AND MANAGEMENT FOR NON-FUNGIBLE TOKENS

RELATED APPLICATIONS

This application is a continuation in part of U.S. application Ser. No. 17/531,746 filed Nov. 20, 2021 which in turn is a continuation in part of U.S. application Ser. No. 17/531,598 filed Nov. 19, 2021 which in turn is a continuation in part of U.S. application Ser. No. 17/344,043 filed Jun. 10, 2021 which in turn is a continuation in part of U.S. application Ser. No. 17/230,911 filed Apr. 14, 2021 which in turn is a continuation in part of U.S. application Ser. No. 17/176,056 filed Feb. 15, 2021 which in turn is a continuation in part of U.S. application Ser. No. 17/128,084 filed Dec. 19, 2020 which in turn is a continuation in part of U.S. application Ser. No. 16/997,840 filed Aug. 19, 2020, which is a continuation in part of U.S. application Ser. No. 16/994,585 filed Aug. 15, 2020 which in turn is a continuation in part of U.S. patent application Ser. No. 16/991,916 filed on Aug. 12, 2020 which in turn is a continuation in part of U.S. patent application Ser. No. 16/876,080 filed May 17, 2020 which in turn is a continuation in part of U.S. patent application Ser. No. 16/810,782 filed on Mar. 5, 2020 which in turn is a continuation in part of U.S. patent application Ser. No. 16/510,634 filed on Jul. 12, 2019 (now U.S. Pat. No. 10,713,737 issued Jul. 14, 2020) and U.S. patent application Ser. No. 16/510,642 filed on Jul. 12, 2019, which are all incorporated by reference. Patent application Ser. Nos. 16/510,542 and 16/510,634 are both continuations of U.S. patent application Ser. No. 16/452,076 filed Jun. 25, 2019, which all are incorporated by reference.

BACKGROUND

1) Field of the System

A system for verification and management of non-fungible tokens (NFT) that are assets themselves, digital asset, or a digital asset paired to a physical asset. A NFT can be paired to a physical article such as collectibles and memorabilia and be a virtual representation that has a verified link to the digital or physical asset to create a undichotomized pair that can be used for authentication, verification, anti-counterfeit, appraisals, auditing, recording and the like. The system can facilitate management and reporting the status, activity, and transactions associated with the NFT and paired items that are physical articles, such as collectibles, memorabilia, photos, artwork and the like or are digital items. The digital asset can be an NFT or can represents an NFT.

2) Background

There has been a significant increase in the use of NFT as the number of digital assets created and traded increases. For example, one NFT for digital art has sold for as much as $69 million, social media posts from a well know social media platform first posts sold for #2.9 million and even a well-known toilet paper company has created and placed five pieces of digital art up for bidding. The digital art states that it is the world's first Non-Fungible Toilet Paper. There is even an effort underway to convert patents into non-fungible tokens to commercialize on a "rareness" or "uniqueness" of the NFT.

As with physical assets a buyer is typically willing to pay a higher price for unique items. The issue with digital assets is that virtually identical copies can be may which generally decreases the value due to a lack of uniqueness or originality. In economics, this is referred to as scarcity value. A scarcity value is an economic factor reflecting an increase in an item's relative price by an artificially low supply. Therefore, having the ability to reduce the number of "official" digital assets would be of commercial benefit. Further, whereas the prices of newly made items generally reflect the cost of production, certain items such as antiques, rare stamps, sports memorabilia, collectibles derive value from the scarcity of the item itself.

With an NFT, it would be advantageous for the buyer to know that the digital asset is authentic without having to rely upon trust between the parties. Without this trust will, the value of the asset (digital or physical) can be reduced or eliminated. A system that relies upon trust, especially unverified trust, is not as desirable as one where reliance on trust is eliminated and replaced with verifiable truth. Such a system is needed to provide the parties to a transaction improved value for the asset (digital or physical) and can reduce or eliminate the risk of fraud.

As digital asset can be easily copied and one attempt to prevent fraud is by using NFTs. Common counterfeits are made and distributed for counterfeit artwork, sports memorabilia, autographs, wine, jewelry, and others. Once authentication company reported that in 2012 it analyzed approximately three hundred and fifty thousand autographs and discovered that autographs that were not authenticated were over fifty percent (50%). Media articles have reported that fraud is expected in somewhere between 50 to 80% of all memorabilia. Fear of fraud affects consumers or originators of the digital asset significantly by decreasing consumer confidence and lowering values due to concerns over authenticity.

In some markets, protection against counterfeits includes authentication of articles which can take time and money and in some cases is not practical. Another method of reducing the risk of counterfeit is for an article to have "paperwork" or a Certificate of Authenticity (COA). Unfortunately, there are counterfeit COA's and some unscrupulous makers will counterfeit the article and then provide the counterfeit asset with a counterfeit COA. Further, the COA has become misunderstood and the mere fact that a seller provides a COA can mislead the buyer into believing that the article is authentic. Even were the COA to be authentic, the COA should accompany every purchase of an article and include detailed information about the article. For example, a COA for artwork should include detailed information such as artist name, title of the work, year of completion, dimensions, medium, edition number (if applicable), any special instructions and a sample or complete image of the artwork.

As for NFT, there have been reports of sales of counterfeit NFT's to unsuspecting buyers. The issue was with the creation of the NFT and that the seller purported to state that the NFT was created by a certain person when in fact it was not. An NFT was reported to be up for sale by a British street artist and was sold for over $500,000. Subsequent to the sale, the buyer believed that the sale was of a counterfeit NFT which was confirmed by the street artist. Therefore, a system for the authentication and verification of a NFT at its creation of prior a transaction is needed. Having such a system helps reduce or eliminate the ability of the public to be deceived by counterfeits and is a problem which deserves much attention.

There have been attempts to create digital assets and tokens as shown in United States Publication 2020/0242105, but these attempts failed to verify the authenticity of the NFT as its source at creation of prior a transaction. There has been some attempts to use biometrics with NFT such as in United States Application Publication 2021/0256070, but these system do not verify the NFT is authentic.

With digitization, an article such as a physical article or digital time such as a photograph, video, and the like can be converted into a digital representation such a digital file and stored on a database. In the current systems, especially with digital representations and COAs, there is a significant risk of scams, frauds, and irregularities with the articles. Further, a significant disadvantage with current digital systems is the potential for rehypothecation. Hypothecation means posting an asset as collateral for a debt so that in the event of a default, the asset can be seized (e.g., foreclosure or repossession) to satisfy the default at least partially on the debt. Rehypothecation is when the creditor uses the collateral from a first loan (e.g., original loan) and uses it as collateral for a second loan. Rehypothecation increases uncertainty and adds risk in that actual ownership, lien, or collateral can become uncertain. Digitization alone does not provide a solution as there is no ability to insure that the digital representation of the object or event. Further, mere digitization does not provide information such as data directed to when, where, who or what was or is associated with an object or event. Even certificates of authenticity have been shown to be susceptible to fraud.

There is also an issue with a chain of title or custody for articles such as collectibles. Current systems have a lack of accountability, verification and reliability of information related to the article and transactions. The inability to verify or authenticate articles and other factors can result in loss, mistakes, increased insurance claims, fraud, and increased insurance premiums. While there have been some attempts to add item information to a physical material, such as U.S. Pat. No. 8,321,302, these attempts have focused on tracking inventory levels and do not include verifiably pairing a physical material with a virtual representation that can be tracked throughout a process. Further, these prior attempts focus on a single location and do not consider the fact that the physical location of the article can be at separate locations. This disadvantage can be seen in U.S. Pat. No. 8,521,620 which specifically states that if a RFID tag is lost or damaged, the system allows a user to enter an item number or style and tags of similar items are displayed, a new tag is generated and associated with the item having the lost or damaged tag. Once the RFID tag is lost or damaged, the physical asset is no longer associated with the virtual representation. While this system specifically allows for the replacement of RFID tags on the same item, it lacks the ability to verifiably pair the new tag with the physical asset.

The disadvantages of current systems are caused in part due to the lack of verification at creation to determine of the digital asset promised and delivered are a same. Attempts to provide for inspections (e.g., authentications) that a digital asset is original have not solved the existing problems.

There is also a need to verify that the individuals or organization during the creation, authentication, and transactions of digital assets and that they are who they say that they are.

There is a need to verify the location of where a transaction takes place, especially when the digital representation represents an article and any event that it memorializes, what the article is, and what parties were involved with its creation and subsequent transactions.

There is also a need to verify that the actions being performed by the individual are in compliance with applicable standards, regulations and other requirements. Specifications in some processes can include the specification of an authentication process, commercialization process of other performance criteria of the article. Specifications can include initial registration and transaction requirements and notifications.

It would be advantageous to have a system that verified digital assets including NFTs, authorized individuals and that associated assets and tasks are properly digitally represented. Pairing the digital asset with an individual, time and location at its creation, during or associated with an event, such as when it became a memorabilia item, increases the value, reduces, and potentially eliminates fraud and promotes increased truth in the object and its related events and transactions. Further, pairing digital assets with a creator, event, individual, team or a transaction can include immutably recording the life of the object, events, activities, and transactions provides for improved ownership transfers in perpetuity.

It would be advantageous to have a system that reduced or eliminates the risk of a counterfeit, fraud, substitute, lesser quality or other non-designated or approved article being used. It would be advantageous for a system that prevented or reduced the risk of counterfeit, unlicensed or unauthorized articles. It would be advantageous to have a system that allows for third party or automated independent verification to reduce counterfeit, fraudulent, false, or misleading information and activity.

A system whereby the inspector is uniquely identified in the asset record to identify the inspector including the time, location and biometric identifier for the inspector would be advantageous. For example, in the collectible market, the inspection may occur after the event that generated the digital asset so that there is no ability to completely verify that the digital asset is the one that is associated with an event (e.g., an image of the xxth homerun ball).

It would be an advantage to have a system that can verify a digital asset at its creation or before its first transaction so that authentication can be easily and quickly accomplished in real time.

It would be advantageous to have a system that provides for multi-party, multi-system verification of the digital asset for tracking of the digital asset through transactions.

It would be advantageous to have a system that provides for a verified trustworthy association between digital asset in an immutable record.

It would be advantageous to have a system that provides for a verified trustworthy digital asset association with a physical object that is stored on an immutable or persistent ledger.

SUMMARY OF THE SYSTEM

In accordance with an exemplary embodiment, this system can include a computerized system for verification and management of a digital asset can include a computer system disposed at a use location and in communication with a persistent storage; a sensor in communications with the computer system; a set of non-transitory computer readable instructions included in the computer system adapted for: receiving a digital asset from a creator of the digital asset; receiving significant information wherein the significant information is taken from a group consisting of date, time, event, individual, team, organization, notation, and any combination thereof; receiving identification information using the sensor of the creator; retrieving location information representing a physical location where the identification information is received, and the computer system is located; retrieving date and time information from the computer system; creating a digital asset record that includes a unique identifier associated with the digital asset, identification information, location information, and date and time information; storing the digital asset record on the persistent storage.

The unique identifier can be created according to an origination record and the significance information wherein the origination record represents a creation of the digital asset. The origination record can include information of a first individual confirming significant information and associating the significant information with the asset. The origination record can include a manufacturing information associated with a physical asset represented by the digital asset. The use location can be included in the digital asset record and is taken from the group consisting of a sporting stadium, physical asset manufacturing facility, distribution facility, sales location, gallery, studio, IP address, digital asset creation location, and any combination thereof. The origination record can include a raw material information representing a raw material used to make a physical asset associated with the digital asset. The raw material can be the material from which sporting equipment is made or other such information. The origination records can include a manufacturing verification information representing that a manufacturer physically verified that the material used in the physical asset is the same material used in a design associated with the physical asset.

The digital asset record can include an attribute record information representing the attributes included in the digital asset. The attributes can be taken from a group consisting of duplicability, interactivity, networkability, variability and compositeness. The significance information can include biometric information of an individual verifying that the asset is associated with an event as well as biometric information of an individual associated with the digital asset. The significance information includes biometric information of an event associated with the digital asset.

The event can be taken from the group consisting of a sporting event, political event, entertainment event, transaction event, signature, autograph, nostalgic event, and any combination thereof. The significance information includes biometric information of an individual during a transaction associated with the digital asset. The significance information can include information associated with a creation of the digital asset.

The set of non-transitory computer readable instruction can be adapted to retrieve the digital asset record, receive a buyer information, receive a seller information, associate the digital asset with a transaction according to the buyer information and the seller information, create a transaction record according to the transaction, digital asset record and a transaction verification information. The transaction verification information can be taken from the group consisting of a biometric information of the buyer, biometric information of the seller, buyer identification, verification of the seller, verification of the asset and any combination. The verification of the asset can include capturing an image taken of the asset at a transaction location, transaction date, transaction time, transaction event, buyer, seller of any combination thereof. The transaction location can include a location marker associated with the location; and the computer system is uniquely paired with the transaction location using the location marker.

The set of computer readable instructions can be adapted to create a buyer record representing the buyer of the asset and storing the buyer record on the persistence storage. The set of non-transitory computer readable instructions can included creating a digital asset record using the sensor representing a physical asset associated with a digital asset wherein the digital asset is included in the digital asset record and includes physical asset information taken from the group consisting of date, time, event, team, individual, notation, and any combination, creating a significance record using the sensor having significance information taken from the group consisting of date, time, event, team, individual, notation, and any combination, associating the significant record with the digital asset record, and storing the digital asset record on the persistence storage.

The digital asset record and the associated significance record can be configured to be retrieved from the persistence storage from a third-party computer system and adapted to verify that the physical asset is authentic according to the asset record and the associated significance record. The computer system can be contained in a device taken from the group consisting of a kiosk, tables, laptop, portable device, smart phone, and any combination. The digital asset can include a unique identifier.

The set of non-transitory computer readable instructions included in the computer system adapted for: creating a digital asset record according to the digital asset adapted to be identified by the computer system, storing the digital asset record on the persistence storage, creating a transaction record representing a transfer of the digital asset from a first entity to a second entity wherein the transaction record includes a transaction verification wherein the transaction verification includes seller biometric information, seller biometric information, date, time and location associated with eh transaction, transmitting a payment request according to the transaction verification to a second entity account representing payment for the digital asset from the second entity to the first entity, and, storing the transaction record on the persistence storage.

The first entity can be an originating entity, and the second entity can be a buyer. The digital asset record can be created according to an origination information representing physical verification of the location of a physical asset associated with the digital asset. The digital asset can be digital art. The digital asset can be a virtual representation of a physical object wherein the virtual representation is associated with a physical object.

Paired can include use of an immutable record that includes information such as a digital asset, object, individual and transaction anchor to a location. The record can include immutable time data, biometric confirmations, unique identification of the object, and metadata from data such as images of other data associated with the object, individual, date, time, location, and truncation. One form of location anchoring it is to a global position system and include the location (include geolocation) coordinates of the object, parties, and transaction. Further, specifications of the object itself could be recorded in the immutable digital asset record.

The origination record can include information of a first individual creating or witnessing significant information and associating the significant information with the digital asset. For example, an official at a game can physically collect the video or image of the xxth homerun ball, either during or after the event, enter it into the system with the significant information of the xxth homerun so that the digital asset is verified and the digital representation is authentic. The use location can be taken from the group consisting of sporting stadium, digital asset creation facility, physical manufacturing facility, transfer facility, distribution facility, sales location, gallery, studio, IP address and any combination thereof. The location may be verified through a location anchoring using the computing devices associated with the creation of the paired digital asset record. For example, the GPS coordinates of the computer device use to creation the digital asset can be included in the digital asset record. Additionally at the time of recording the immutable record can be immutably recorded.

In the event that the digital asset is paired with an object, the origination record can include a material information representing the components used to make the digital asset, associated physical asset and a manufacturing verification information representing that a manufacturer physically verified that the components used are the same material used in a design associated with the digital asset. The digital asset record can include a material information representing the material used to make the digital asset. The material information can include physical (raw material) or digital (equipment used to create the digital asset). The significance information can include biometric information of an individual verifying that the digital asset is associated with an event. The significance information can include biometric information of an individual creating or otherwise associated with the digital asset. The event can be taken from the group consisting of a creating the digital asset, sporting event, political event, entertainment event, transaction event, signature, autograph, nostalgic event and any combination thereof. The significance information includes biometric information of an individual during a transaction associated with the digital asset. The significance information includes information associated with a creation of the digital asset.

Further, previous owners may be identified by wallets commonly used in the block chain or crypto currency industries. Current owner may also be identified through a wallet tied to a biometric or other known identification method. Previous and current owners could be stored in the digital asset record to ensure authenticity in a continuing ownership and or association chain of the object. When a digital asset is sold to a new owner a new event that would record when, where, referencing the unique identification of the digital asset, and the parties involved who would be by metrically or other known confirmations. Recording of the series of events would ensure that when the digital asset or associated object is sold that the new owner can be assured that it is in fact the authenticated object. These digital assets could be sold on exchanges that were related specifically to the governing body of specific sports or event, such as the NFL or event places like Madison Square Garden.

The system can be managed and governed by an auditing function that would verify the immutable recording as well as the integrity of the data and look for anomalies to further prevent fraud or give certificates of authenticity of truth related to the item.

BRIEF DESCRIPTION OF THE DRAWINGS

FIG. 4 shows various types of biometric data that may be gathered.

FIG. 5 shows the types of events that may be triggered.

DETAILED DESCRIPTION

Figure 1B:
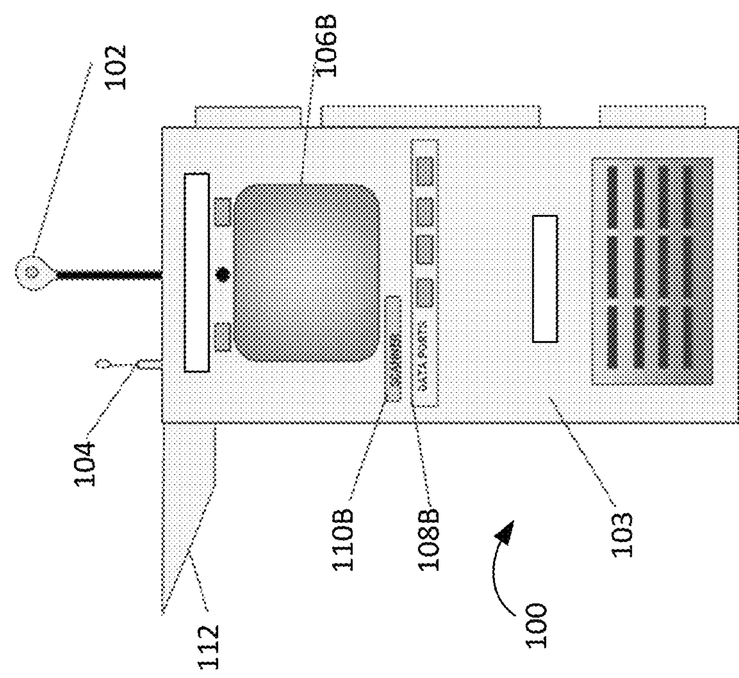
FIGS. 1A-1F shows various side views of aspects of the system.

The present system provides for verification of digital asset including non-fungible tokens (NFTs) and increase transparency with the digital asset, associated physical object, ownership, authentication, transactions, and the like. The system can include a server or kiosk that can include a set of server computer readable instructions configured to receive information about a digital asset including the ability to capture information such as the description of the digital asset, manufacturer, characteristics of the digital asset such as if it new, used, signed, unsigned, limited edition, special run, material specifications of the object and the like, an event associated with the digital asset such as it if is associated with a game, event, auction, and the like, its significance, or description, such as if it is an image or video of a xxth home run ball, xxth win, xxth game and the like, the individuals associated with the digital asset such as players, teams, coaches, date and time, location, individuals that can verify or certify the generation of the digital representation and the meta data associated with that activity. Significance information can be any information that could distinguish the digital asset from other like assets. Significance information can include date, time, activity, event, locations, individual, team, record, notation, and any combination. For example, the event could be an end of season event, a notable event (e.g., first time to the World Series, first home run, etc.), pre-season, regular season, and the like. A notation can be a digital signature or image of an autograph, physical signature, label, or other addition to the digital asset. For example, the image of the baseball for the $600^{th}$ homerun that is digitally signed by the batter may have a larger value than one unsigned. The significance information can be validated which can be performed by the system and/or one or more individuals (e.g., inspectors) as well as verified with associated metadata.

For example, the system can capture an image of an object of event and that can be the digital asset, including its unique identifier and associate that information with an individual, date, time, and location. The digital asset can be an immutable digital asset wherein the immutability can be present at the creation of the digital asset or can be added to the properties of the digital asset after its creation. For baseball, a batter information can be captured that can include images, video, date, time, and location information of the batter. An inspector, human automated or a combination, can visually inspect the digital asset and its association with significant event and batter and verify that the digital asset and individual were at the location at the same time. The system can retrieve scheduling and occupancy information and verify that the inspection and the batter were at the same location at the stated date and time. Digital assets can be compared with environmental information (e.g., weather) information at the location, date, and time so that the background of an image showing the environmental conditions can be compared with third party weather information. If the digital asset shows a cloudy date and the third-party weather information shows a cloudy day, the confidence of authenticity of the digital asset increases. Biometric data can be capture from the batter, creator, official, inspector or others as well as attendance information from access control system to verify that the individual were at the use location at the date and time the virtual representation is created. The location can also be verified from the location anchoring of computing devices, and the time of the event can be immutably verified and recorded against an immutable storage system such as blockchain or other chain type storage systems.

This information captured can be stored in a record that include fields associated with the above as well as make, model, quantity, warrant information, class, type, or other identification of the digital asset, one or more sources, the cost, care instructions, material specifications, other materials that can be included and other information.

For example, the material can be an image of a baseball that was used in a game and signifies some event, such as a xxth hormone or xxth strike out or xxth hit. The original certifier can create one or more digital asset records representing one or more digital assets representing objects used during an event or process or task that can involve the digital asset, the location, an event, individuals, or other aspects. For example, Team 1 can be playing Team 2 and the digital asset can be an image of a baseball representing the xxth hit by Team 1 against Team 2. The baseball can also be associated with an individual (e.g., player, independent of the team such as the players xxth hit or homerun. The digital asset can be associated with a record or other memorialized event such a team record being broken. The associated records can be stored on a persistent storage platform that can be accessed by multiple parties. The persistent storage can be disposed at the location of the creation of the digital asset, event, individual, process, or assembly or can be remote from such location. For example, a stadium can have a kiosk with the computer readable instructions that can record the digital asset (e.g., receive or capture an image) and the date, time, event, individual, etc. and store the information in an original digital asset record. The certifier or other individual can have the individual information recorded (e.g., biometric information) so that there is a record that the certifier created the record with an identifier of the digital asset at a certain time and location so that a record is created pairing a digital asset with a physical object or event to pair the digital asset with the physical event.

The system can also provide the digital asset record to a third-party such as an online store, retail location, auction, distributor, or reseller that can deliver the digital asset to a transaction location, virtually or physically. A third party such as a buyer can review, and potential acquire the digital asset. The third party can review the digital asset record and determine if the digital asset specified is authentic. For example, as with verification of the digital asset with the significance information, the transaction can be verified by capturing the creator, date, time, location and other information about the digital asset. An image of the buyer and seller and the digital asset can be captured by the system and compared with third-party information such as occupancy, attendance, weather, and other information and if the third-party information is consistent with the transaction information, confidence in the authenticity of the transaction and digital asset increases. For example, if an access control system shows the buyer at the location when the transaction occurs, a significative event occurs of other activity so that the confidence of an authorized is increased.

The third party can be a buyer, insurance company, certifier, authentication company and the like. The digital asset record can be stored on the persistent storage so that the originating and subsequent confirmation and transaction information cannot be subsequently altered or tampered with. The digital asset record can include a virtual representation of information associated with the physical asset. In one embodiment, the digital asset can be specified by class, type, product code, product number of other identifying information and virtual representation.

The digital asset record can include creation location, transaction information or other information showing that the life of the digital asset. For example, the digital asset record can include the creation location, serial number, date transmitted, and date received. The digital asset can be created for a significant event. In the United States, the Super Bowl can have specific game balls that are design and used specifically for the end of season game. An image of the game balls with one image per ball can be turned into a NFT that can be associated with an indicator on the game ball such as an RFID tag. When one or more digital asset records are included on the persistent storage, along with the other records described herein, an audit trail can be created that is based upon the collection of records on the persistent storage. Therefore, when a NFT is sold of a game ball, authenticity and confidence in value is increased.

When a digital asset is selected for transfer, a transferring company (e.g., shipping company) can be sent a shipping order representing the digital asset to be transferred from one storage media to another or held on the persistent storage. The shipping company can be provided shipping information from the manufacturer, designer, supplier, or other company that can facilitate the transaction (e.g., broker, distributer, reseller). The shipping order can be provided directly to the shipping company or can be retrieved from the persistent storage. Once the shipping company receives the shipping order, it can transmit the desired digital asset and determine if the digital asset in the shipping order match the digital asset at the current digital asset location. A shipping pickup record can be created representing that the shipping company transferred the digital asset and that the digital asset received matches the shipping order. This verification can be independent of the other verifications described herein. The data associated with the object or digital representation can be used by a smart contract associated with the transfer of the object and shipping record to facilitate a commercial transaction between a buyer and seller.

Once that asset is transferred to the recipient, the shipping company can verify that the digital asset was properly transmitted or transferred and that the it was the same digital asset included in the shipping order. This can occur through autonomous computing systems that scan and compare and analyze the unique identification numbers as well as the originating location and time to the corresponding delivery time and location data and using analytics verify the probability of certainty that the item could have been transferred. The immutable digital asset record could be then updated autonomously or through input devices. The shipping company can create a shipping delivery record representing that the digital asset was transmitted or transferred and that the digital asset matches the shipping order. The shipping delivery record can be stored on the persistent storage. Receiving entity can review the delivered digital asset and verify that the delivered asset matches the creation, design, digital asset requirements, supply record, shipping order, shipping pickup record, shipping delivery record or any combination.

Once the digital asset is received by the desired location, the system can notify individuals that the transaction is complete. The individuals can be verified by the system and an individual verification record can be created and stored on the persistent storage. The system can utilize biometrics or other systems as described herein for verification of actual individuals at the creation location confirmation to correspond with requirement for those that can verify that the digital asset is authorized. For example, in some sports only image and video taken by the team or league are allowed. The digital asset can be determined to have attributes such as proper creation, no unauthorized modifications, and the like.

The system can identify individuals creating or verifying the digital asset and store this information on the persistent storage. The verification can be through biometric identification devices such as a camera or other image capture device, facial recognition, voice recognition, retinal scans, fingerprint scanners, hand scanners, and other biometric devices. In one embodiment, the computing logic may allow authorized individuals to manually enter the presence of another authorized individual, including on the controller at the use location or through a remote device that can be determined to be at the use location, within a boundary associated with the use location, in proximity to the system. In one embodiment, individuals may be verified and paired with a virtual representation using two-factor authentication.

The individual can be provided with user information and specifications or other design requirements that can be represented by a task record. The task record can be stored on the persistent storage. Once installed the system can verify that the digital asset was properly created, stored and transferred (which can be individually inspected) according to the task record, create a task verification record and store the task verification record on the persistent storage. The task verification record represents that a task associated with the digital asset was properly completed. The task record can represent that the task was performed by proper individual and in compliance with any requirements as well as if the digital asset passes one or more inspections.

Prior to, during, and after a task is completed, an inspection can be performed that can include a pre-task inspection, task inspection, post task inspection and any combination. A pre-task inspection, task inspection, and post task inspection record can be created so that the three records can be stored on the persistent storage. The task record can include information that the inspection resulted in passing, passing with deficiencies, and failing. If the inspection fails, the official, team, participants or players or other entities can be given the opportunity to remedy the failure and the inspection process can be performed again. The process can also determine if, while the task passed the inspection, the deficiencies should be remedied. For example, a digital record is created of the xxth homerun, but the digital record does not include an image of the team's logo. The digital image could be updated to reflect the team logo for so that the digital asset is complete.

The system can be uniquely associated with the use location. A location marker can be affixed to the user location and uniquely identify the user, object, event, or other relevant data origin location. The use location can be an event location (e.g., stadium, arena, track, school, gallery, manufacturer, distributor, etc.), auction, trade show retail shop, business, and the like. The location marker can be read by the system so that the system can determine its location. Third parties can read the location marker to determine the location. Other parties can access the location marker to verify that the third party is at the use location. Such access can be through hardware communications which as LTE, 5G, Bluetooth, WiFi, and other wired and wireless communications. Information can be captured form personal devices of individuals including device ID number, date, time, locations, and the like. Such device information can assist with a determination of when and where an individual was at a time of an event or transaction. In one embodiment, digital assets can be transferred from the seller one at a physical location, to a buyer who completes the transaction at the physical location of the seller. In one embodiment, the location of the seller can be matched with the digital asset creation (e.g., the sporting event) so that a digital asset that is not originating from the seller's location may have a lower confidence level and therefore value. This information can be immutable recorded and associate or included in the digital asset record.

The system can be contained in a housing such as a kiosk and can be physically associated with the use location. The use location can be defined by a boundary representing the perimeter of the use location. The system can include a sensor and reader which can be selected from the group consisting of radio frequency identification (RFID) detector, ultra-high frequency (UHF) detector, a bar code scanner, a QR code scanner, near frequency communication (NFC) device; Bluetooth beacons, an optical character recognition (OCR) device and any combination thereof. An environmental sensor, such as a weather sensor or weather station, can be in communications with the or included in the housing and configured to record the weather and other environmental conditions at the use location and at different times during the project. This information can be used to verify the authenticity of the digital asset.

The system may record the date and time of events such as the creation and transfer of the digital asset, individuals, player, audiences, participants officials, third parties, inspections, and the like to and from the use location, the date and time associated with environmental conditions including weather. Recording environmental information, including weather, at the use location allows for autonomous confirmation of environmental conditions that do not rely solely on third party sources or sources that are general or distant from the use location. For example, if a digital asset record is associated with a particular game the environmental condition of that event can be recorded so that subsequent authentication can match the purported event location, date and time and weather conditions at that location, date and time to determine if there is a match.

The individuals on the use location may be prompted to wear certain wearables that provide useful information to the system. For instance, individuals may be prompted to wear location tracking devices, such as GPS devices, Bluetooth, radio frequency identification (RFID) devices, ultra-high frequency (UHF) and/or beacon-based devices. The use of the wearables helps to perform geofencing within the use location which can in turn assist with authentication of the digital asset. The location tracking provided by the wearable helps the system to monitor the location of individuals on the use location on an ongoing basis. The permissions may define what portions of the use location an individual may access. Ongoing monitoring may indicate that an individual is attempting to enter a location where the individual is not permitted. This may trigger a response as described herein. A signal may be sent to the vest or wearable to trigger a visual or audio cue that the individual is not in a permitted area. In addition, individuals may be requested to wear wearables that track biometric information, such as heart rate, body temperature, respiration rate and blood pressure. This information may be tracked and stored on an ongoing basis.

The system may allow for the establishment of one or more geofenced zone that can be associated with use location and location of the creation of a digital asset. These locations can include entrance areas, exit areas, event areas, storage areas, and any combination thereof. The system can assist with verification that digital asset stored at these locations are consistent with the information concerning the digital asset status, locations, state, etc.

The system, including a controller, may also interface with individuals to allow for the entry of notes and related details of a material, task, inspection, environmental condition individual, other task, process of individual or any combination thereof. For example, the system may allow an inspector to capture images of notes, forms, documents, labels, and the like using various readers, sensors, and input devices. The system can capture the creation of the digital asset such as during a game, on the sideline, etc. Event and occurrences that can add significance to the digital asset can include foul balls, homeruns, wins, loses, records (e.g., xxth hit), plays and any number of events or occurrence that are associated with a digital asset.

Smart contracts may be provided that use the persistent storage for each event of the digital asset is transferred the ownership and payment can execute upon satisfaction of terms of a transfer event. For example, when a digital asset is delivered from a shipper to a use location and a verification of the digital asset with is virtual representation occurs, this event can trigger a smart contact that instates payment to the shipper. When the digital asset is transferred from one owner to another, the system can recognize the transfer, update the digital asset record with new ownership or custody change, record the transaction, and automatically initiate payments or other funds transfer. Smart contracts can be used to create a digital asset that can be valued and traded itself. For example, the digital representation of a player signing in xxth baseball can be a digital asset, have its own independent value, be subject to verifications (e.g., capturing date, time, location, individual, IP address and the like), subject to the verification herein and stored on the persistent storage. For example, a digital photo of an event (e.g., player signing a baseball) can be captured and that digital photo can be the digital asset. Photos of significant occurrences at an event which might not include any other physical object than the participant can become a digital asset. The photo could include GPS anchoring in the metadata time verification through block chain or other persistent storage hashing biometrics of the originator as well as biometrics of the subject of the photos. These photos could be authenticated and given digital asset numbers which would prove originality, prevent reproductions, and reduce or elimination counterfeits.

FIGS. 1A-1D illustrate an example of a system 100 that can be a kiosk of other housing that can be uniquely associated with a use location in an exemplary embodiment. The housing can be a housing that can be affixed to the use location. In FIGS. 1A-1D, the system is implemented as a kiosk that can be mobile and include a housing having a controller. The housing 103 may be located at a use location and include a controller in communications with a computer readable medium. The housing can be physically associated with the use location, virtually associated with the use location or both. A location marker can be affixed to the use location such as in a concrete slab or otherwise affixed at the use location. The housing can be removeable attached to the use location so that it is stationary during a first project or process but can be moved to a second project or process at a different physical location once the first project or process is completed. For example, the housing can be positioned at a trade show for collectibles or memorabilia transactions during that trade show and removed at the conclusion of the trade show.

For a location marker, in one embodiment, a transmitter such as a RFID can be associated with the use location by embedding it is a permanent fixture. The system can read the information from the location marker and associate its actual location with the use location. The location marker can include an alpha, numeric or graphical information such as a number, letters, barcodes, QR code, physical, plaque, sigh or geographic coordinates (e.g., GPS coordinates), passive transmitter, active transmitter, and the like. Each system can have a unique identifier and each use location can have a unique identifier.

Figure 1A:
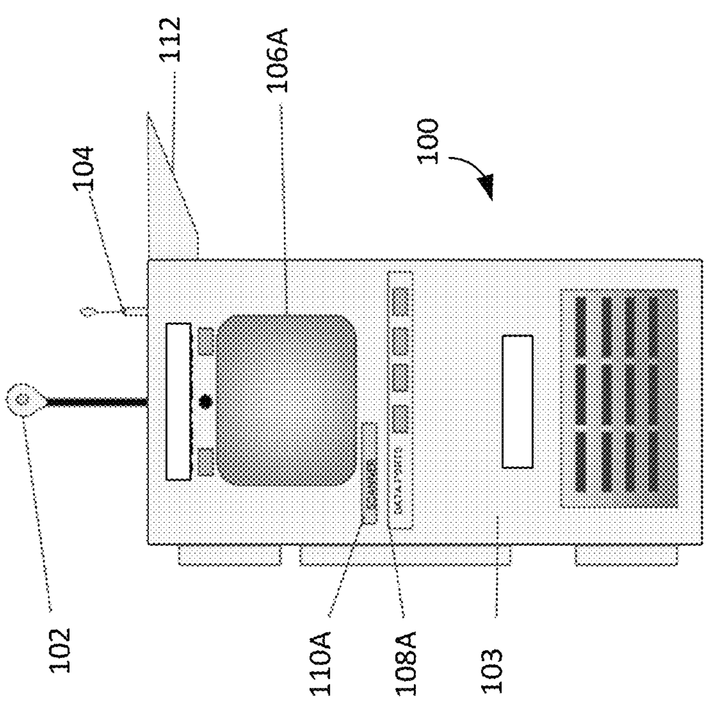

FIG. 1A shows a first side of the system 100. The system 100 can include a camera 102 for creating images including images of physical assets, individuals, or other items at, entering, or leaving the use location as well as images of individuals along a perimeter. The camera 102 may capture biometric images upon which biometric recognition may be performed. Multiple cameras may be placed on or around the housing. The cameras may have biometric recognition and motion detection capabilities. System 100 may include an addition to the camera 102 or instead of the camera 102, biometric-based identification devices that may be used to confirm the identity of individuals entering, leaving or on the perimeter of the use location. The system 100 may include an antenna 104 for communicating with a network including a wireless network, Wi-Fi network, Bluetooth, quantum networks, cellular network (e.g., 4G or 5G network) and any combination. The system 100 may include a housing 103 made of suitable weather resistant material, appropriately sealed to protect the internal hardware. The system 100 may include a display 106A, such as a touchscreen display, upon which the digital asset, information and other data may be displayed and entered. The display 106A may include an integrated camera that may be used to capture images and that may be used in performing facial recognition of individuals. The display may also include or operatively associate with one or more integrated speakers for providing audio output, a microphone for receiving audio information to facilitate two-way communications to a remote location. The system 100 may include a scanner 110A for scanning items, such as deliveries, as will be explained in more detail below. The scanner 110*a* may be, for example, a QR scanner, an Optical Character Recognition (OCR) or a bar code scanner 110A in some instances. The side of the system 100 shown in FIG. 1A can be used for inspections. An inspector may review or enter images of inspection information and documents via the scanner 110A or camera and may interface with the system using the touch screen display 106A. In some embodiments, there may be fewer sides in which to interact with the system for all authorized personnel. An overhang 112 may be provided to assist in decreasing glare and protecting some of the items on the housing from the weather. The above components can be included in a sensor assembly in communications with the controller.

FIG. 1B depicts a side of the system 100. This side can include a touch screen display 106B as well as a scanner 110B. Display 106B may include or be operatively associated with an integrated camera for capturing images, speakers for providing audio output and a microphone to facilitate two-way communications with a remote location. Still further, this side of the system 100 may include data ports 108B.

Figure 1D:
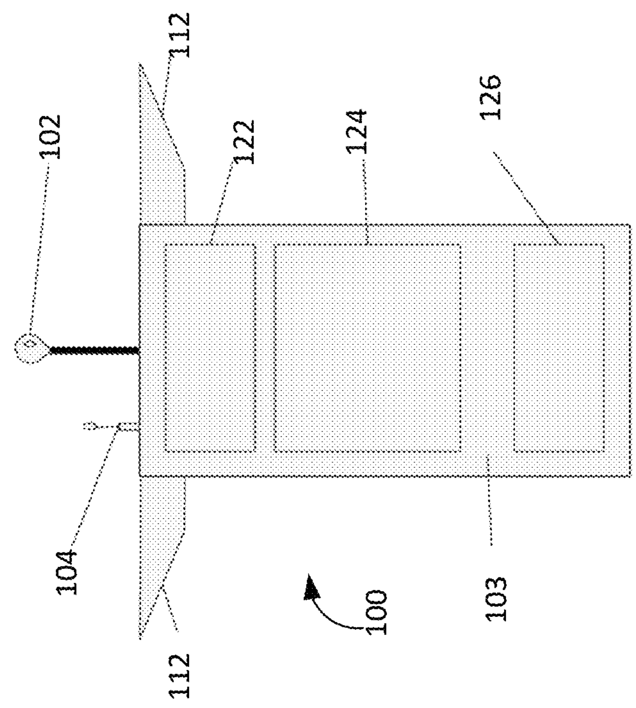
Figure 1C:
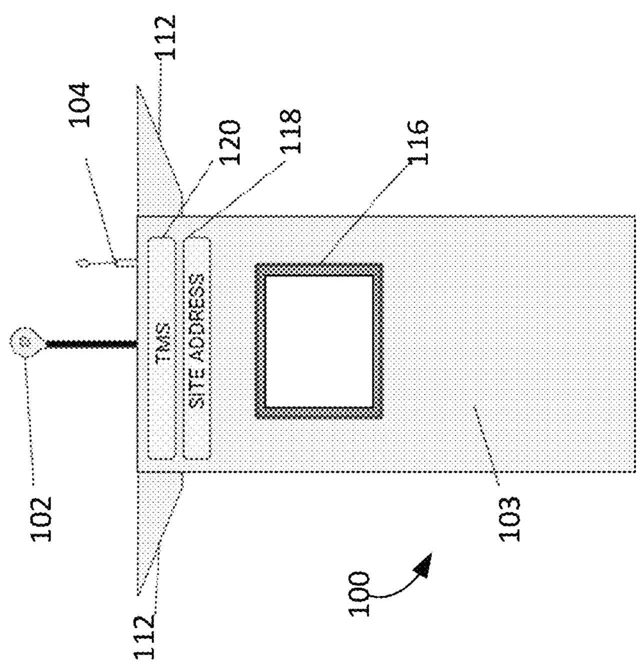

FIG. 1C shows a third side of the system 100. This side has a location 116 in which information such as certificates, bill of sale, receipts, tax information, and the like and may be displayed. In some embodiments, the information displayed may assume electronic form so that a video display is provided in the area 116 of the housing 103. In one embodiment, the unique identifier can be a number 120 for the use location may be displayed on the housing 103. Other location identifying information can be displayed such as location number, store number, assembly number, trade show number, verification number, certification number, use location and the like. In addition, the site address 118 may be displayed on the system 100. The site address may refer to both the mailing address for the use location and/or other physically identifying information associated with the location.

FIG. 1D shows a side of the system 100. An access panel 122 may be provided to access a breaker box for the system 100. An additional access panel 124 may also be provided to access internal components of the system 100.

Figure 1F:
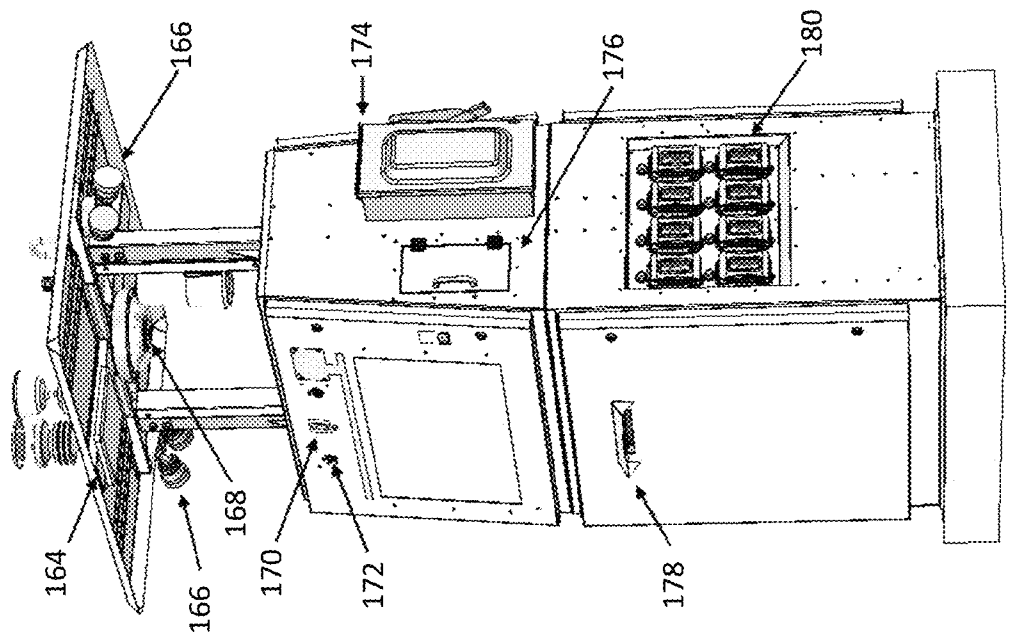
Figure 1E:
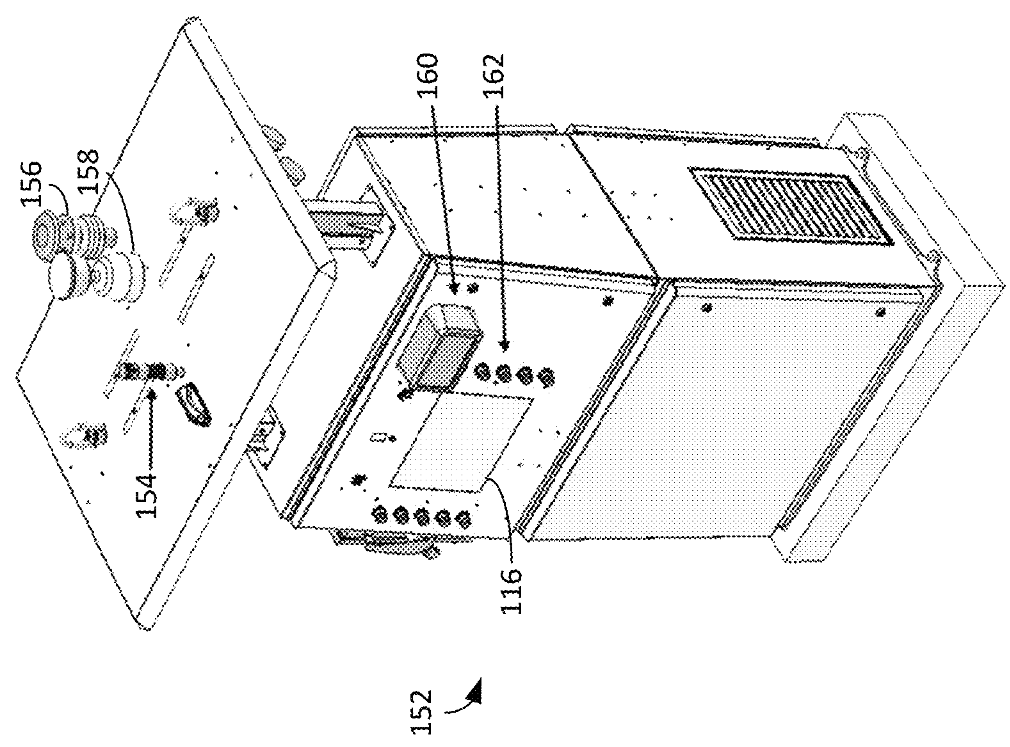

Referring to FIGS. 1E and 1F, the housing 152 can include a side that is configured to be used by an individual at the use location. The housing can include an alarm indicator 154 that can be actuated as described herein. The housing can include a weather station 156 that can include an integrated or separate fluid (e.g., rain) collector 158. Biometric reader 160 can include an iris scanner, fingerprint scanner, palm print scanner, facial scanner, or some combination. Display 116 can be proximity to input assemblies such as buttons 162. The housing can include a field receiver 164, lights 166 and camera 168. One or more cameras can provide a 360° field of view and include a wireless connection for transmitting images to a remote computer device. The images can also be inputted into the system including input allowing the system to identify delivered materials and/or objects. In the instance that a digital image is a digital asset the system can be used to recognize an individual, photographer, entering the field and the like. The system can include one or more second cameras 170 such as webcams disposed at various locations around the system for capturing images. The lights can include motion activation and photoelectric activation. Speakers 172 can be included to provide audio information to a user, inspector, or other party using or near the system. The audio information can include instructions, alarms, and the like. Power junction 174 can include a shut off switch that can be used in emergency and non-emergency situations. The system can include a secondary power source, such as a battery, so that when the main power is shut off, an alarm can sound, notification send to a remote computer device of other indication that the system or power source has been powered down. The system can include a hand scanner (not shown) that can be protected by a hand scanner access door 176. A document scanner 178 can be included in the system for receiving physical documents, converting the physical document into a digital representation, and storing the digital representation on the computer readable medium or the persistent storage.

Figure 1G:
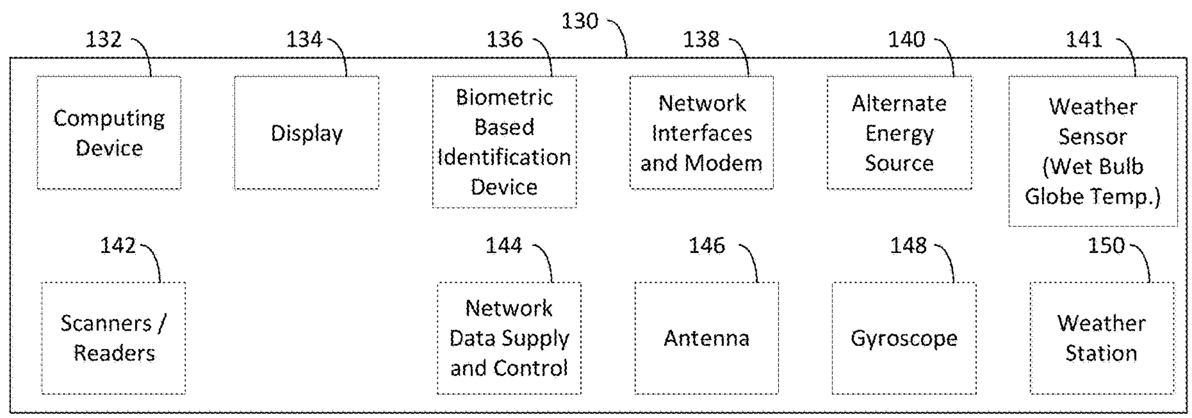
FIG. 1G is a block diagram of components of aspects of the system.

FIG. 1G depicts components that may be included in the system of exemplary embodiments even when not included in the housing. The system may include a computing device 132. The computing device 132 may take many different forms indicating a desktop computing device, a laptop computing device, a mobile computing device, an embedded system, a smartphone, special computer device, custom computer device, or the like. A display 134 may be integrated with the computing device 132 or as a separate device, such as a liquid crystal display (LCD) device, a light emitting diode (LED) display device or other types of display devices on which computer information may be displayed. One or more biometric-based identification devices 136 may be provided. As will be explained in more detail below, multiple biometric-based identification devices may be used. Network interfaces and a modem 138 may be provided. The network interfaces may interface the computing device 132 with a local area network or a wide area network wherein the networks may be wired or wireless. A transceiver or other communications assembly can be included allowing communications with remote computer devices. For example, when a digital asset is created representing an event such as the xxth homerun, a portable computer device that has its own location information and is associated with this system and kiosk, can be used to record the digital asset and its represented object, event, individual, date, time, location and other data described herein to create a record that can be immutably stored. The system can be a portable computer device that can be assigned to a location during the transaction of other activity associated with the object or asset.

The system 130 may be implemented in a distributed fashion and may include an alternative energy source 140. For example, solar panels, wind turbine(s), a battery or the like may be used. In one embodiment, the alternative energy source may be physically affixed to the housing or in communications with the system or controller. For example, solar panels or a cable to a wind power source could be configured to provide power to the system and/or can be affixed to the system or housing. Alternatively, a power line leading to the alternative energy source may be connected to the housing and system to provide power to the system, housing, and associated components such as external power supplies.

The system 130 may include various scanners and readers 142, such as those described above relative to housing. The system 130 may include an internet data supply control 144 and a mechanism for turning the access to this service on and off under a programmatic control. Programmatic control may be provided to grant or deny access to such resources. The system 130 may include an antenna 146 for wireless communications signals to receive and transmit. The system 130 may include a gyroscope 148 to monitor any moving of the system. The gyroscope 148 may indicate motion indicative of whether someone is trying to move or tilt the housing or other components of the system. Logic may be provided to send a notification in such an event where the gyroscope indicates substantial enough movement. The system 130 may include a weather station 150 to measure current weather conditions, such as temperature, air movement, humidity, precipitation, barometric pressure, direct sunlight, and the like. Input from the weather station 150 may be used to inform decision making by the system in some instances. Alternatively, the weather may be collected via software, such as from a weather service or other weather source.

Similarly, the system 130 may include a weather sensor 141. The sensor can be a wet bulb globe temperature adapted to measure, among other things, heat stress in direct sunlight, which accounts for temperature, humidity, air movement (direction and speed), sun angle and cloud cover (solar radiation). This data can be part of the event or object and associated with the digital asset record.

Figure 2A:
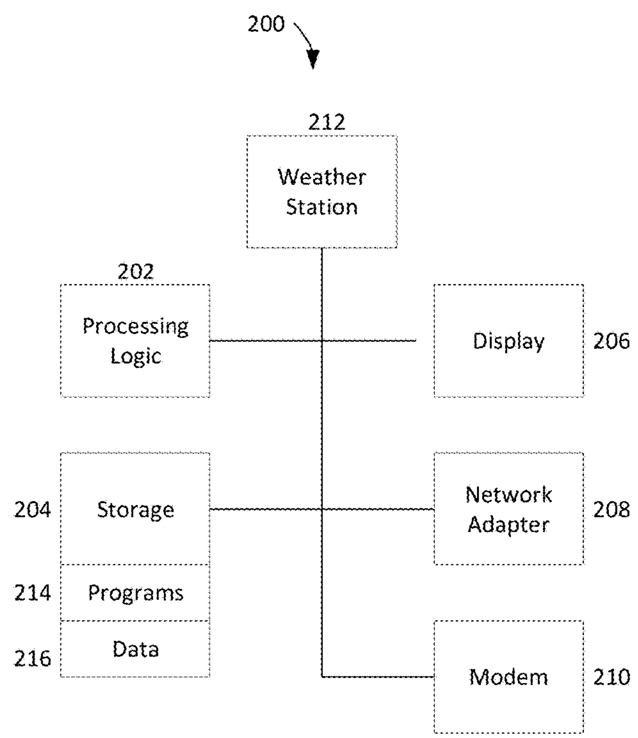
FIG. 2A is a block diagram of aspects of the system.

FIG. 2A shows an example of a computing device 200 for the system. The computing system may include processing logic 202, such as microprocessors, controllers, field programmable gate arrays (FPGA), application specific integrated circuits (ASICs) electronic circuitry, and other types of logic. The processing logic 202 performs the operations of the computing device 132. A storage device 204 may also be provided. The computer readable medium and/or data storage device 204 may take various forms, including magnetic storage, optical storage, etc. Storage capability 204 may include computer-readable media, including removable computer readable media, such as disks, thumb drives and the like, or disk drives, solid state memory, random access memory (RAM), read only memory (ROM) and other types of storage. The computing device may include a display 206, such as an LCD display, an LED display, or other types of display devices on which video information may be displayed. The computing device 200 may include a network adapter 208 for interfacing with networks and a modem 210 for communicating wirelessly, over telephone lines or cable lines with remote devices. The processing logic 202 may use information stored in the storage device 204. In particular, the processing logic 202 may execute programs 214 stored in the storage and may access and store data 216 relative to the storage device 204. The computational functionality of the system described herein may be realized by the processing logic 202 executing the programs 214.

Figure 2B:
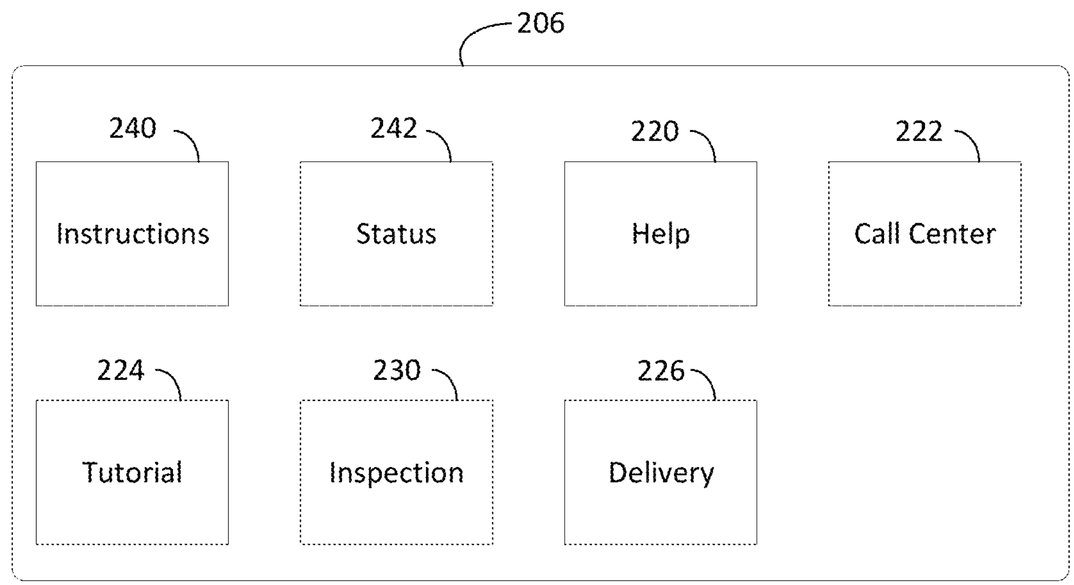
FIG. 2B shows aspects of a user interface.

FIG. 2B shows an example of a user interface on display 206, such as found in the housing 100. The user interface may include activatable elements. A user may depress these activatable elements or select these activatable elements using an input device, such as a mouse, keyboard, touchscreen, or the like, to activate the components. The display 206 may include a help element 220 that may be activated to obtain help information regarding use of the housing. It may also contain real time project or process plans. It may also include "how to" assistance including videos related to the various projects, stages, processes, and tasks performed at the use location. The user interface on the display 206 may also include a call center activatable element 222. Selection of the call center activatable element 222 may cause a call to be initiated with a call center so that the individual using the system 100 may have a telephone and or video conference with personnel at the call center. The call center can be connected to several third parties including a prior authentication individual or entity in the event that communications is needed. The user interface on display 206 may also include a tutorial activatable element 224. Selection of the tutorial activatable element 224 causes a tutorial to be displayed to teach the individual about operation of the housing.

Figure 2C:
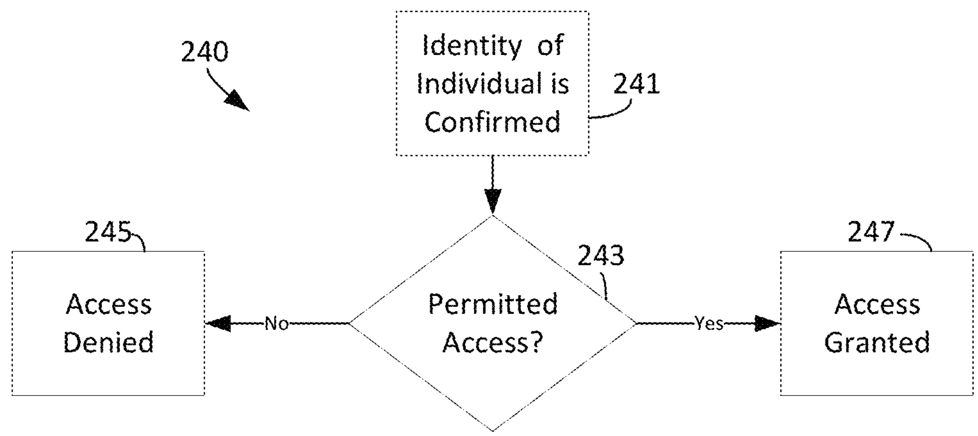
FIGS. 2C-2D show flowcharts of aspects of the system.

Referring to FIG. 2C, the display may show instructions 240 for completing certain tasks or other information. A status of tasks and assets can be displayed at 242. The identity of an individual can be confirmed at 241, such as described above using biometric identity verification. The individual's information is accessed to determine if the individual is to be granted access to create or access the digital asset at 243. If the permissions indicate that access is to be granted, access is granted 247. In contrast if the permissions indicate that access is not to be granted, then access is denied 245. Permission information can be included in the individual information record. Permission information can be retrieved from the persistent storage or the system.

Figure 2D:
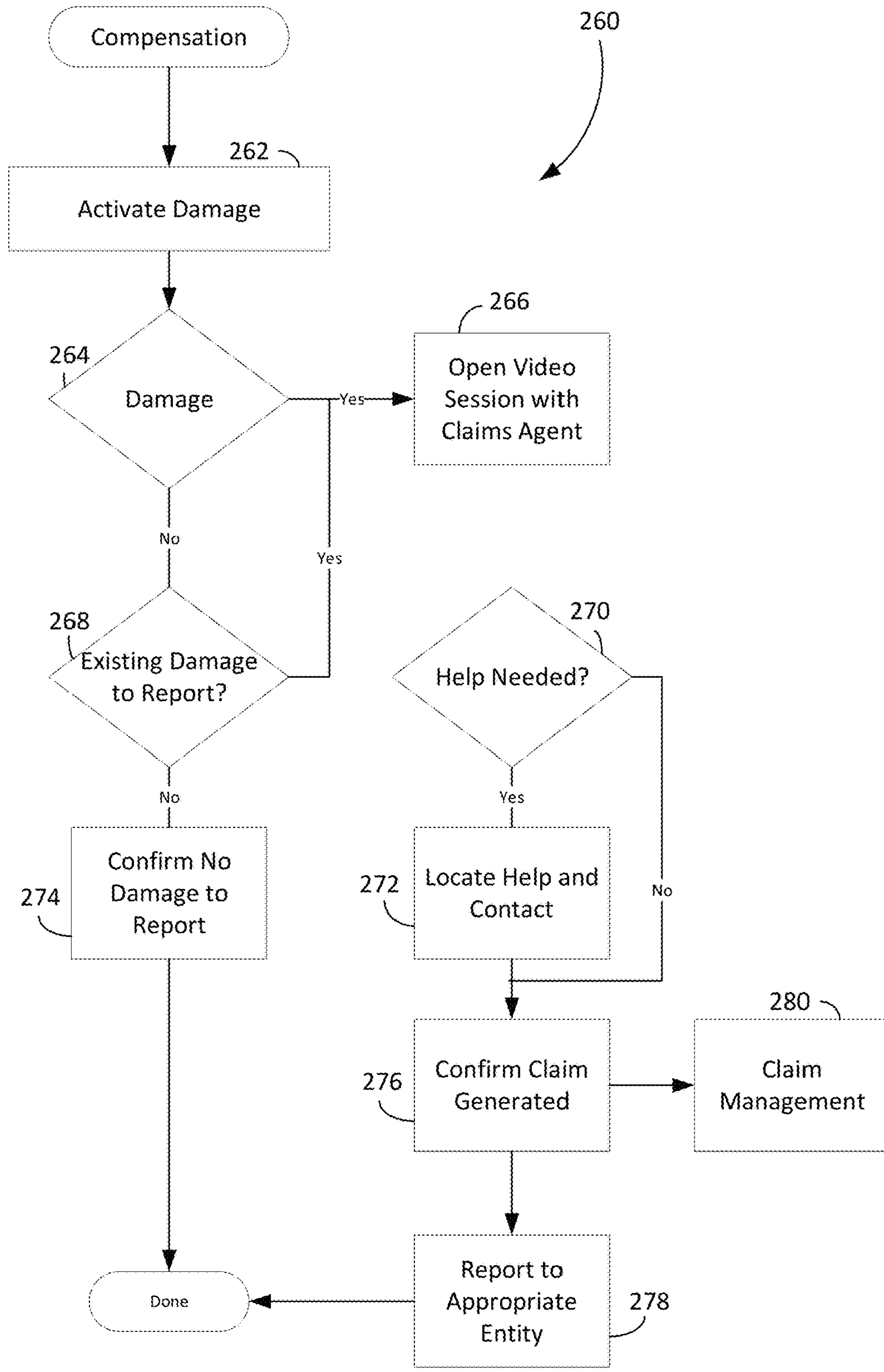

Referring to FIG. 2D, if there is damage or loss of the digital asset at 262, a loss of claim can be made at 264, a video session with a claim agent associated with any insurance on the object and can be initiated at 266. The claim agent may gather information to initiate any claim processing. The claim agent may determine if assistance is warranted 270. If assistance is warranted contact is made with the assistance to be provided at 272. A confirmation of the claim can be generated 276 and sent to claims management 280. In addition, a report may be sent to the appropriate entity or authority at 278. The steps 266, 270 and 272 may also be performed in the instance in which the individual has an older injury to report 268. Where there is no injury to the individual, the lack of injury is reported 274.

Transfer (e.g., shipping or delivery) company personnel may activate the transfer (delivery) activatable element 226 (FIG. 2B). This causes a delivery functionality to be displayed where delivery notes may be added. Objects that might later become paired digital asset could be registered upon their delivery to the specific location. Also relevant to the time they were delivered and their eventual use and memorabilia creation event. This improves authenticity of the digital asset by providing a creation time and location. For example, if the digital asset is an image of a baseball used on a first date but the digital asset record reference a second date, an auditing engine could recognize the anomaly and provide the appropriate record and notifications.

Figure 3A:
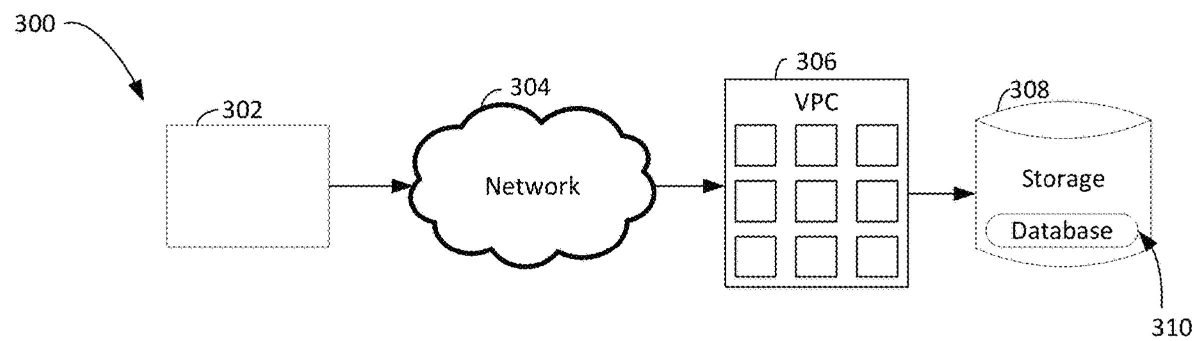
FIG. 3A shows an example of a communications environment.

As shown in FIG. 3A, the exemplary embodiments may be implemented in a decentralized computing environment 300, that may include distributed systems and cloud computing. FIG. 3A shows one or more systems 302 that may be in communication with a remote cluster 306 via a network 304. The cluster 306 may store information received from the system 302 and provide added computational functionality. The network may be a wired network or a wireless network or a combination thereof. The network 304 may be a secure internet connection extending between the system 302 and the cluster 306, such as a virtual private cloud (VPC). The server may be a computing device and can be in communications with the site computer device. The cluster 306 may include access to storage 308. The storage 308 may include a database 310 in which information regarding a use location is stored in a consistent manner.

Figure 3B:
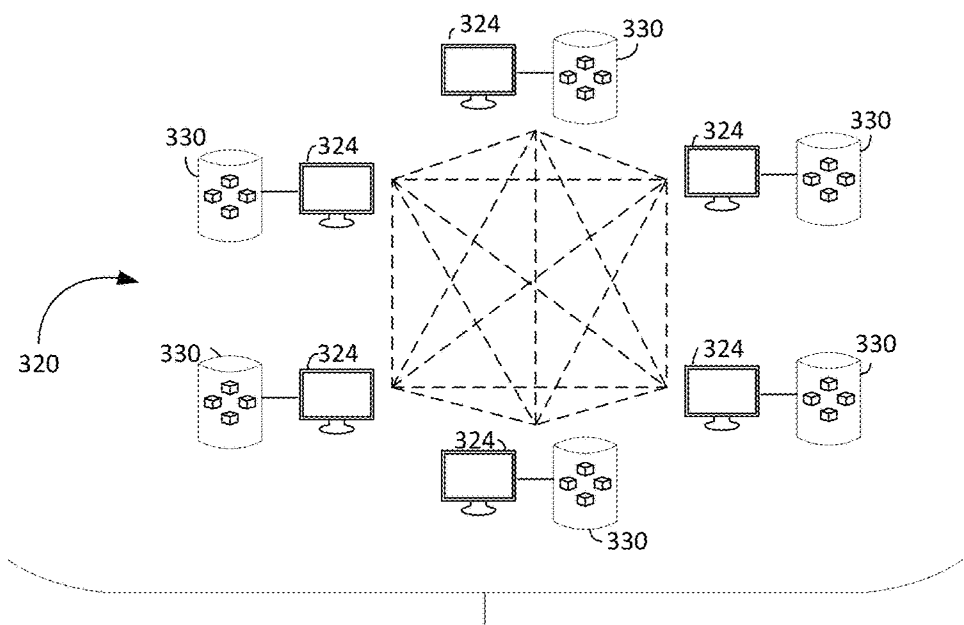
FIG. 3B shows an example of a persistent storage.
Figure 3C:
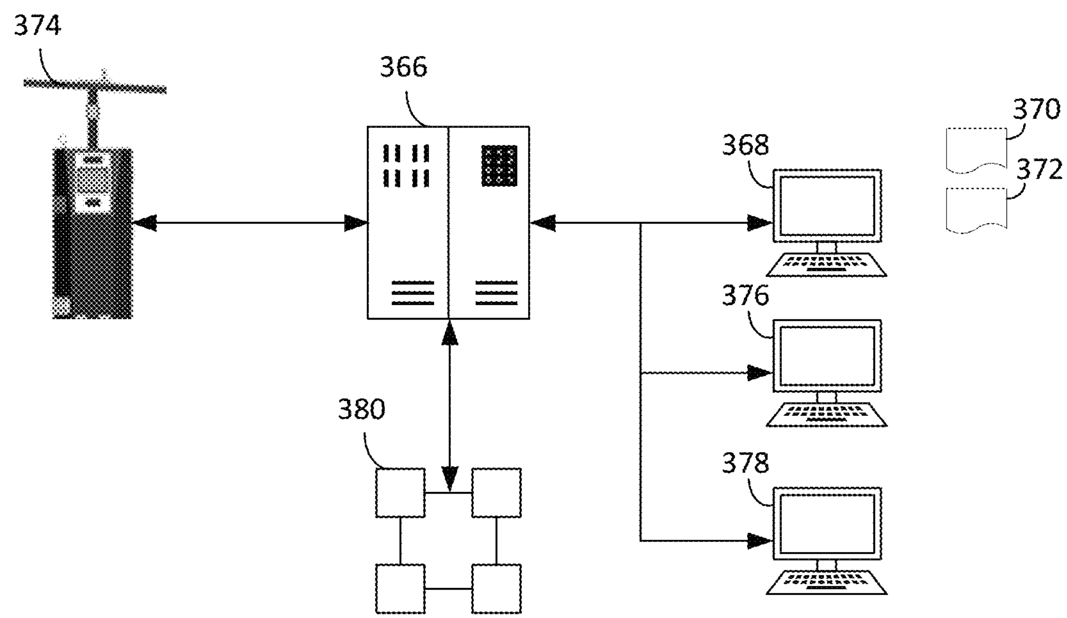
FIGS. 3C-3D show schematics of the aspects of the system.
Figure 3D:
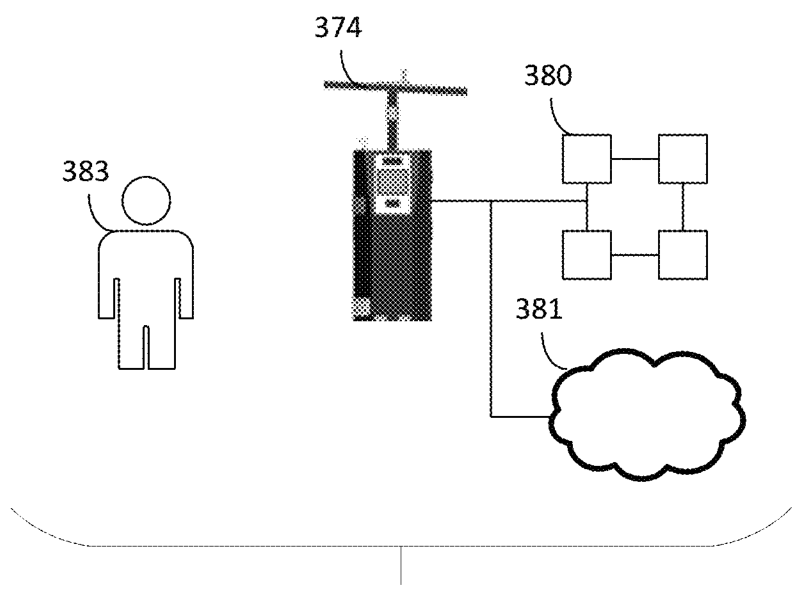

FIG. 3B shows diagram 320 of an example of a peer-based network where a persistent storage 330 is broadcast and shared among the nodes 324. This network may be resident in the VPC cluster 306 (FIG. 3A) or in the network 304 for example. The nodes 324 may represent computing resources, such as server computer systems or other computing systems with storage devices 330. FIG. 3C shows a kiosk 374 in communications with a server 366 that can be in communications with a distributed network 380 or computer, storage devices of any combination. Third party computer system 368, 376 and 378 can be in communications with the server 366 and kiosk 374 so that information 370 and 372 can be shared with these systems. FIG. 3D shows a user 383 using a kiosk 374 to access information from distributed storage 380 as well as transmit and receive data from a global communication network 381.

Processes, projects, and task specifications, which may be needed for compliance with warranty, insurance, design, specifications, inspection, and other requirements, can be received at 376 and requirements can be received from a requirements computer device 378 either directly or from the persistent storage. The requirements can include approved materials that are approved by regulatory entities, such as governments, leagues, manufacturer, teams, players, designers, and the like. Requirements can include specifications, materials, safety codes, and individual licenses, and the like.

The various computer devices, including the server and site computer device (e.g., system, controller, and any combination), can be in communications with persistent storage 380. The persistent storage can include a distributed ledger, immutable database, block-chain structure, and the like. The communications between the various computer device, including the server and the site computer device and persistent storage can be a global communications network, wide area network, or local area network, delivered to a computer readable medium from one device to another (e.g., USB drive, CD, DVD) and can be wired or wireless.

Figure 4:
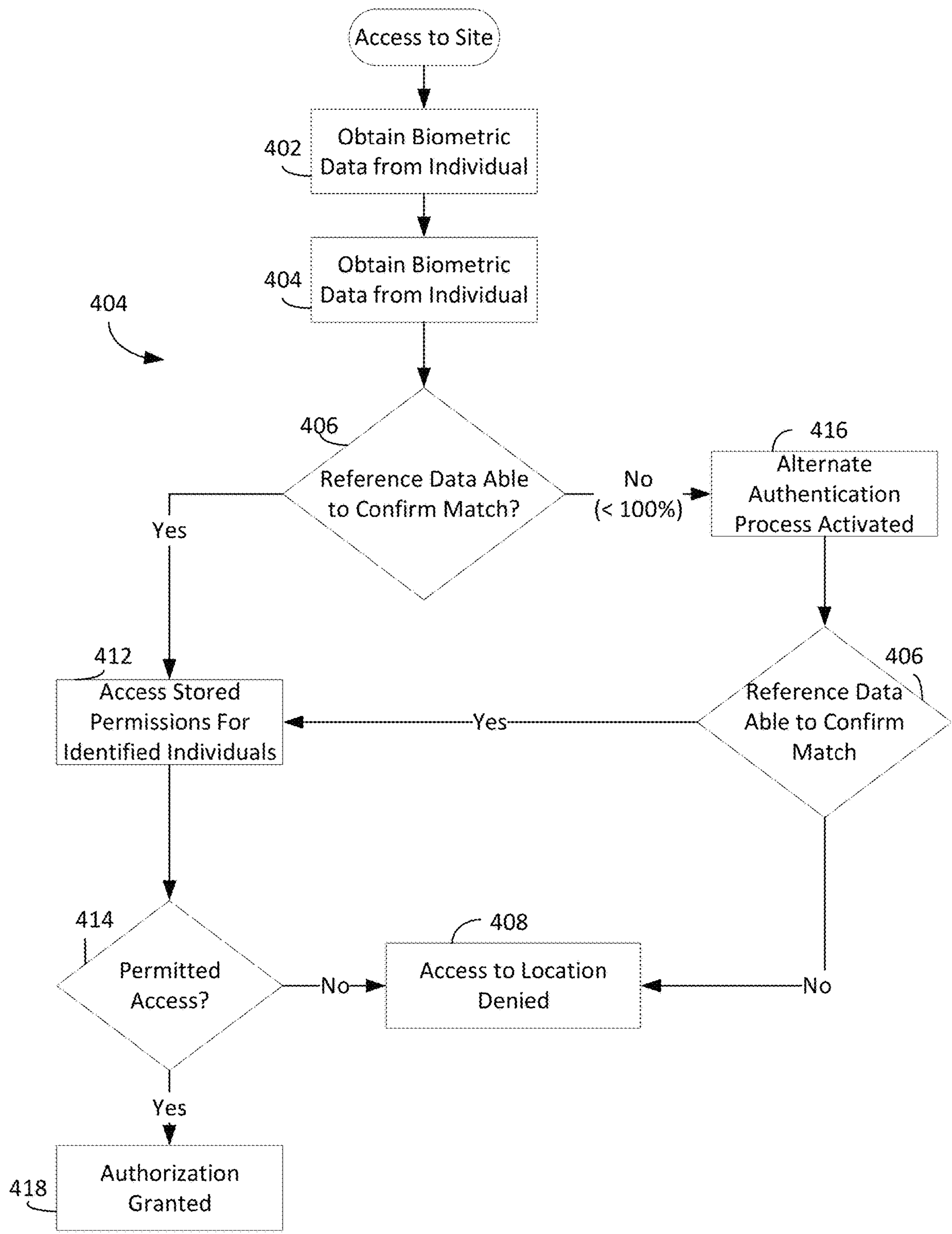
FIGS. 4-5 shows a flowchart illustrating aspects of the system.

FIG. 4 shows a flowchart 400 identifying steps that may be performed in exemplary embodiments regarding this functionality of the system. Initially, biometric data is obtained from an individual or other individual that is seeking access to the system at the use location 402. In some exemplary embodiments, a camera 102 may capture an image of an individual and facial recognition may be performed. The biometric data in one case is the facial image of the individual. In other exemplary embodiments, the biometric data may be, for example, fingerprint data, hand scan data, voice print data, retinal scan data or the like, gathered by appropriate biometric-based identification devices. The obtained biometric data is stored, and then previously stored data is accessed from storage to compare biometric data for known individuals and to attempt to identify the individual 404. A comparison may be made between the gathered biometric data and the known biometric data to determine if there is sufficient closeness for there to be a match. Information regarding the identity of the individuals for which the biometric data is stored is also stored in the storage device. A determination is then made whether there is a match or not 406.

If there is not a match 406, a manual process may be executed, or an alternative authentication process may be deployed 416. If this alternative authentication fails to produce a match 406, access to the use location may be denied or the individual may not be able to create, enter, authenticate or other action associated with the digital asset, object or event at 408.

The system may store permissions for each individual accessing the use location. These permissions may identify the dates and times where the individual is given access to the use location. In addition, the permissions may specify what assets and actions the individual can access or preform. These permissions may be accessed to determine the permissions for the identified individual 412. If the permissions indicate that access is permitted 414, the individual may be granted access to the use location and/or digital asset at 418.

Figure 5:
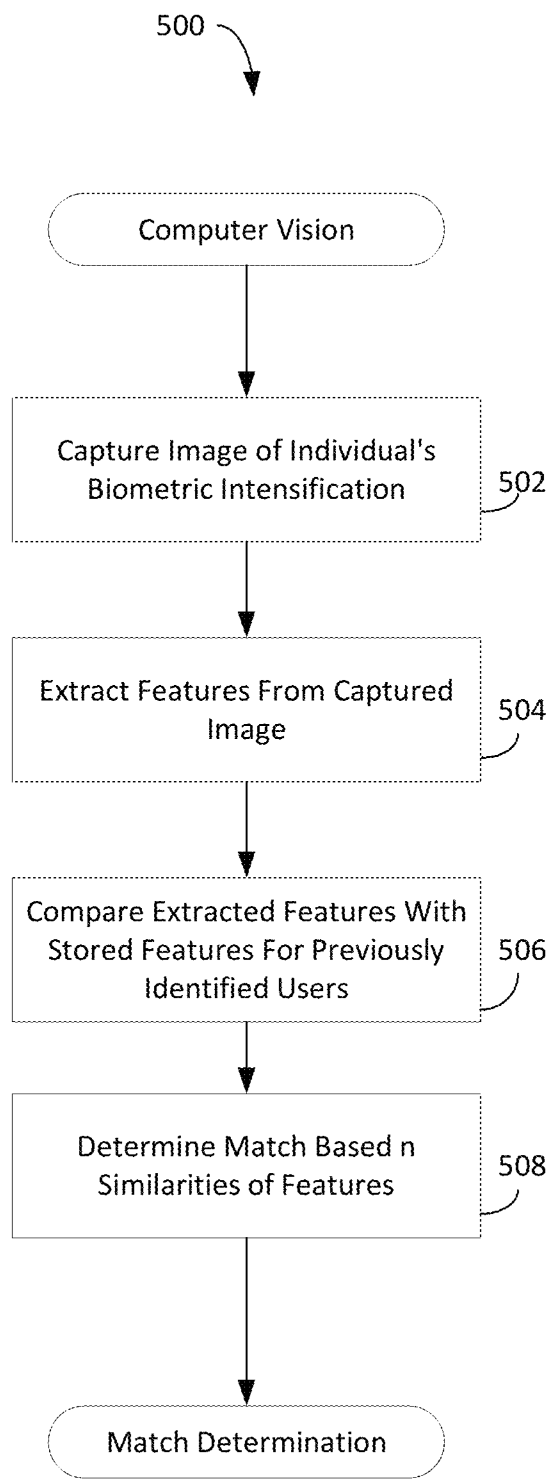

FIG. 5 shows steps that are performed in a case of computer vision for 402, 404 and 406 of FIG. 4. The flowchart 500 begins with 502 in which an image of an individual is captured for biometric recognition. This may be captured by a number of different types of image capture devices, including an intermittent video camera, still camera, iris scanner, facial scanner, fingerprint scanner, or other type of capture device. In the case where an image of the face of an individual is captured, identifying features may be extracted from the captured image 504. In other words, unique facial features that help to identify an individual are extracted from the image. The image may be filtered and/or normalized. The features are then compared with the stored features for identified individuals 506, determination is made whether there is enough similarity for there to be a match.

Figures 6, 7:
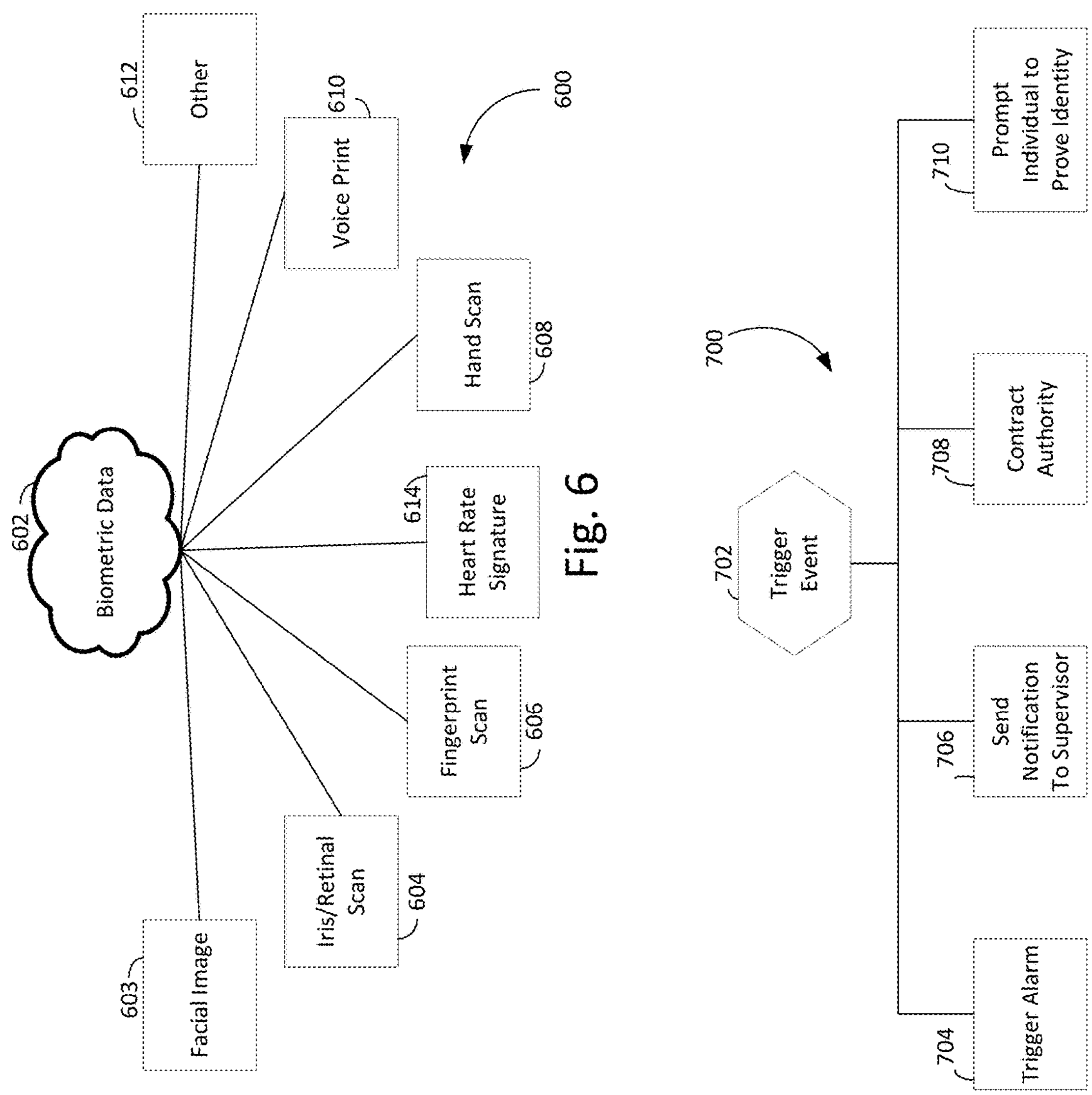
FIGS. 6-8 shows flowchart illustrating aspects of the system.

FIG. 6 shows a diagram 600 that illustrates various types of biometric data 602 that may be obtained by biometric-based identification devices at the use location to attempt to identify individuals. Biometric data may include facial recognition 603, an iris/retinal scan 604, a fingerprint scan 608, a hand scan 608, a voice print 610 or heart rate signature 614. It should be noted that other types 612 of biometric data may also be used in exemplary embodiments to help identify individuals uniquely. Also, an individual may be required to provide multiple types of biometric data in some instances.

When individuals attempt to access the system and is not granted access, certain events may be triggered (see 410 in FIG. 4). FIG. 7 shows a diagram 700 that provides an example of different types of triggered events 702. One type of triggered event is an alarm 704. This alarm may include visual alerts, audio alerts and any combination thereof. The alarm may be a silent alarm to individuals. Another event that may be triggered is to send notifications to a supervisor for the use location 706. The supervisor may, for example, receive an email, a text, a phone call, or another notification that someone is trying to access the site that is not permitted. A triggered event 702 may also include the contacting of law enforcement or a member of a security service indicating that an unauthorized party has tried to access the use location. Lastly, a triggered event 702 may include prompting the individual to produce proper identifying information to an official at the site or to a scanning device at the housing 100.

Figure 8:
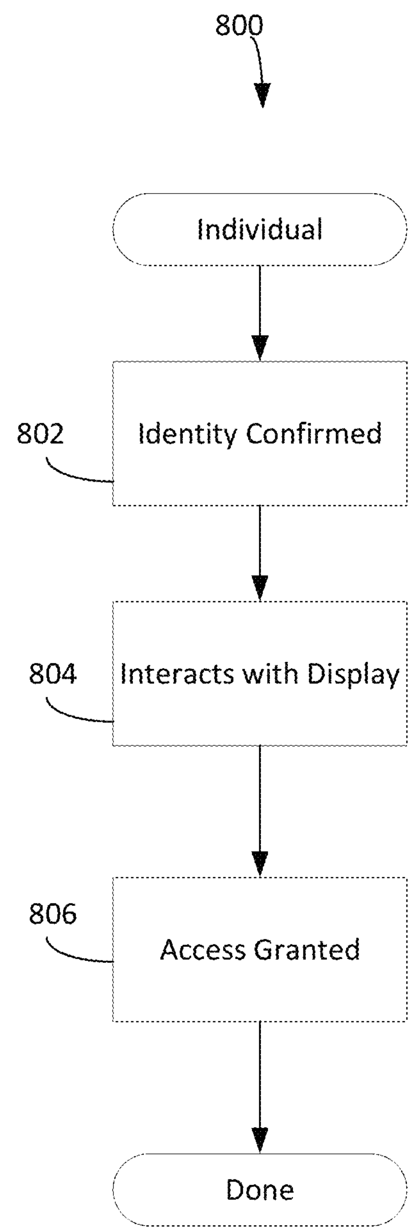

FIG. 8 shows a flowchart of the steps that may be performed to ensure that an individual gains access to the appropriate digital assets or functions once they have been granted access to the system. As shown in the flowchart 800 of FIG. 8, initially the individual has their identity confirmed, as has been discussed above 802. The system may offer an alternative touchscreen option to place a call to the appropriate party should the software fail to verify and otherwise authorized the individual. The individual may be prompted to interact with the display, such as the touchscreen 106B (FIG. 1) to register and to indicate whether they seek certain items.

Figure 9A:
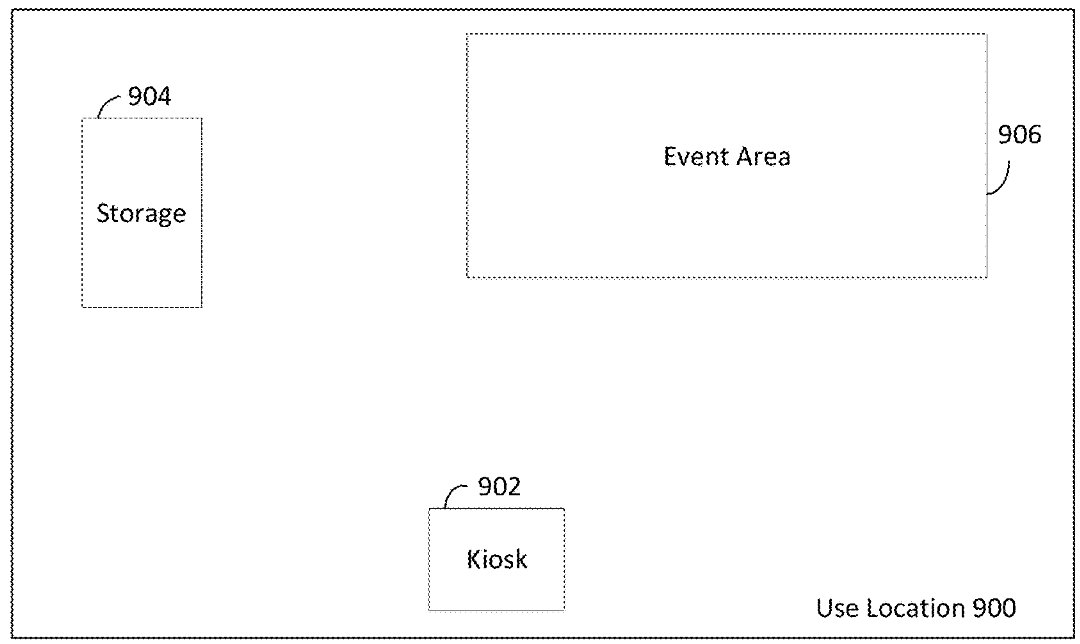
FIG. 9A shows a plan view of a use location.

To help illustrate an example of geofencing, FIG. 9A shows an illustrative use location 900. The use location 900 may include a housing 902 for the system as well as storage location 904 that can be a building, trailer, shed or the like. The storage location 904 may hold physical assets which can include sporting equipment unused or used during an event and/or materials. The use location 900 may also include a task location 906. The task location may be where tasks are performed using materials to create or transact the digital asset.

Figure 9B:
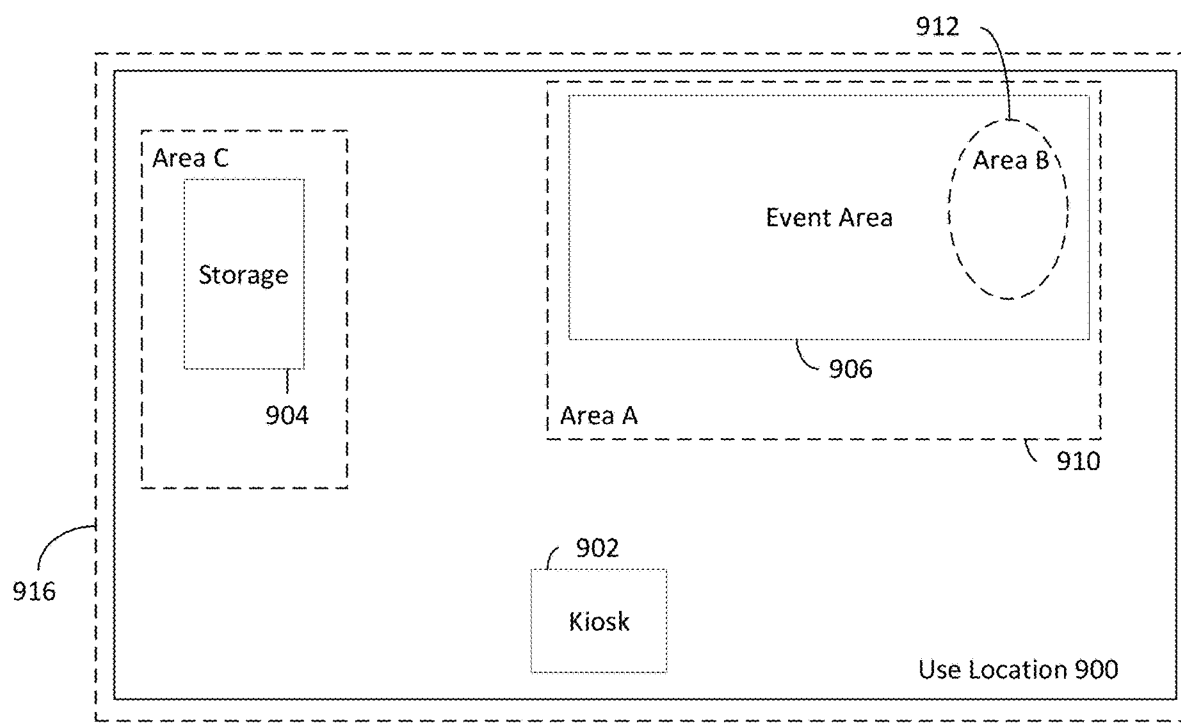
FIG. 9B shows a plan view with geofencing at a use location.

FIG. 9B shows an example of different areas that may be established for geofencing at the use location 900. Area A shown a boundary 910 may include the entirety of a certain use location 906 (e.g., playing field). Area B 912 may be a portion of the use location, such as where physical asset is stored. Area C 914 may be another location and area D 916 may be the entire use location. Individuals may have access to none of these areas or to a subset of these areas, including all areas.

Figure 10A:
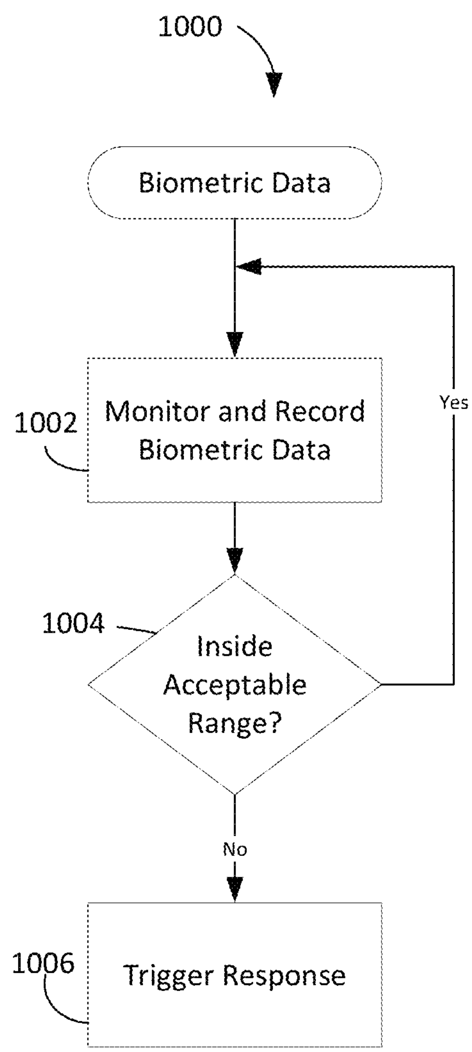
FIGS. 10A-10B show flowcharts is aspects of the system.
Figure 10B:
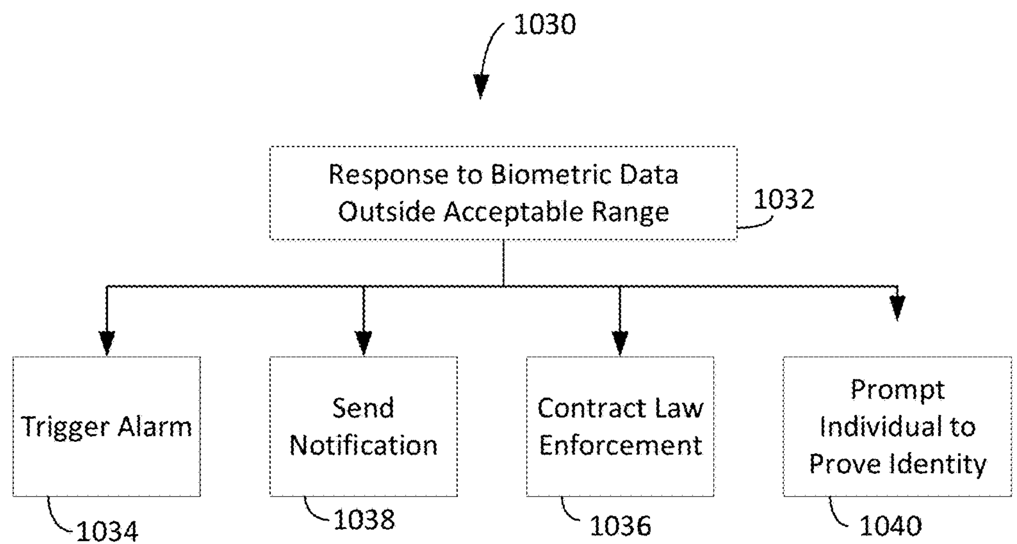

Referring to FIG. 10A, biometric data is capture and recorded as 1002. If the individual associated with the biometric data is not approved to be within an area or to perform a recording or other activity at 1004, a response is triggered at 1006. Referring to FIG. 10B, if the biometric data shows that an individual is outside an acceptable range, an alarm can be triggered at 1032, notification of the alarm can be sent at 1038, law enforcement can be contacted at 1036 and the individual can be promoted to prove his identify at 1040.

Figure 11:
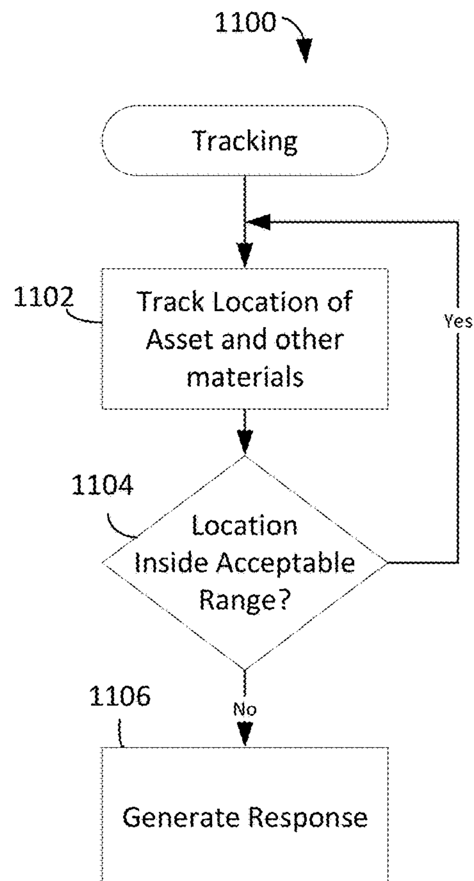
FIGS. 11-19 show flowcharts illustrating steps of the system.

Referring to FIG. 11, the system may track the digital asset at the use location 1102. The system can check whether the creation, transaction or storage location of the digital asset or other materials is acceptable or not 1104. For example, suppose that an owner of an object or other item associated with a digital representation wishes to create an NFT. The owner can capture the object and associate the object with the digital representation and record the data at the kiosk. The NFT then be made available for sale. The system can be disposed at a location where the NFT can be transferred, or the object transferred, and the data associated with the NFT verified and updated. One aspect of the system can be to verify that the location is authorized for a transfer to occur. If the location of the system is not acceptable as checked in 1704, a response is generated in 1106.

Figure 12:
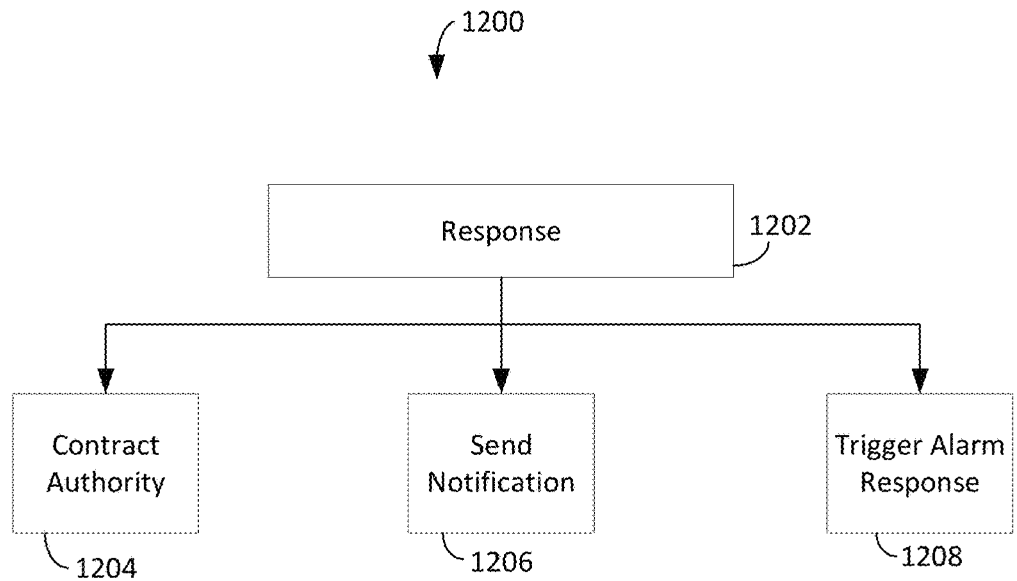

FIG. 12 shows a diagram 1200 illustrating different types of responses 1202 that may be generated in response to the digital asset in an unacceptable state or an unauthorized access to the asset is attempted. One type of response is to contact law enforcement or security 1204. In many cases the notification may indicate that a theft is underway. Another type of response is to send a notification to an individual or to other appropriate parties at the use location 1206. Another type of response is to trigger an alarm response 1208, such as the sounding of an audio alarm or a video alarm.

Figure 13:
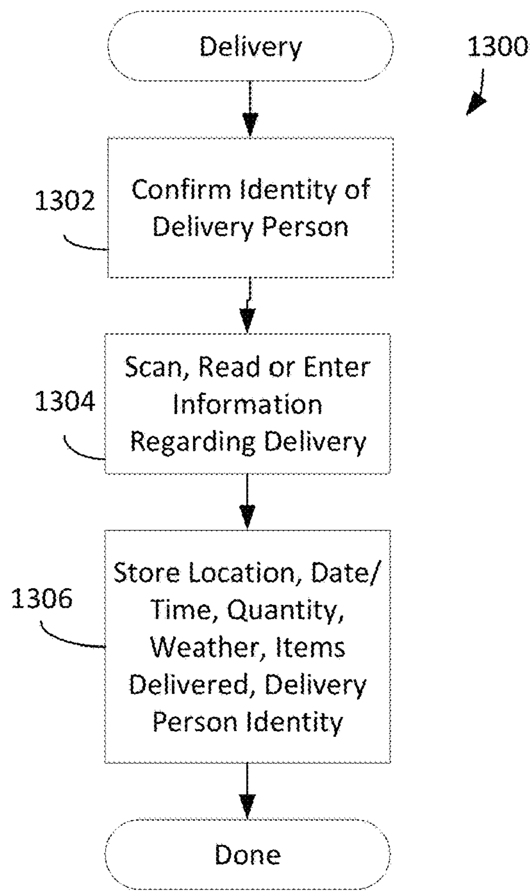

The system helps manage transmission and transfers facilitated at the site. FIG. 13 depicts a flowchart 1300 showing steps that may be performed regarding transfers and transmissions. Initially, the identity of the person requesting the transfer is confirmed to indicate that this person is the appropriate party and is permitted access to the system or use location 1302. In addition, information may be entered by the person using the housing, such as by entering information via screen 106A (FIG. 1A) 1304. The location of transfer, the date of transfer, the time of the transfer, and the identity of the person requesting the transfer may be recorded as part of the information that is kept regarding the transfer. This information can be used to track and confirm transfers as well as to understand the conditions when the transfer was made.

Figure 14:
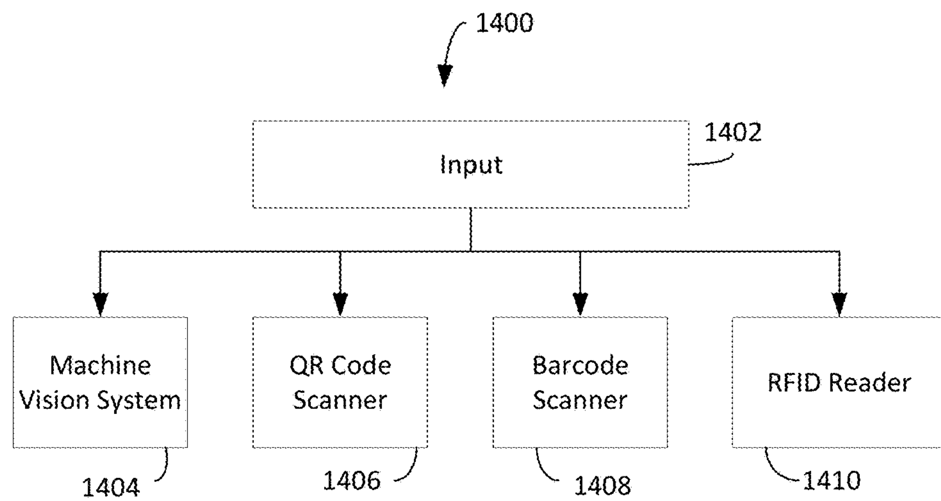

The transfers may utilize various scanning and reader technology. In FIG. 1A, a scanner 110A may be provided. Diagram 1400 in FIG. 14 illustrates different types of inputs 1402 that may be used for assisting gathering information regarding transfers. A machine vision system 1404 may be provided. The machine vision system 1404 may capture information concerning the physical object associated with the digital representation and process the image to determine the nature of the items that were transferred as well as the quantity of items. A QR code scanner 1406 may be used where QR codes are associated with a digital asset or documentation. Similarly, a bar code scanner 1408 may be used where bar codes are associated with the digital asset or on documentation delivered with the items. Still further, an RFID reader 1410 may be provided to gather information regarding the digital asset of object that it represents.

Figure 15:
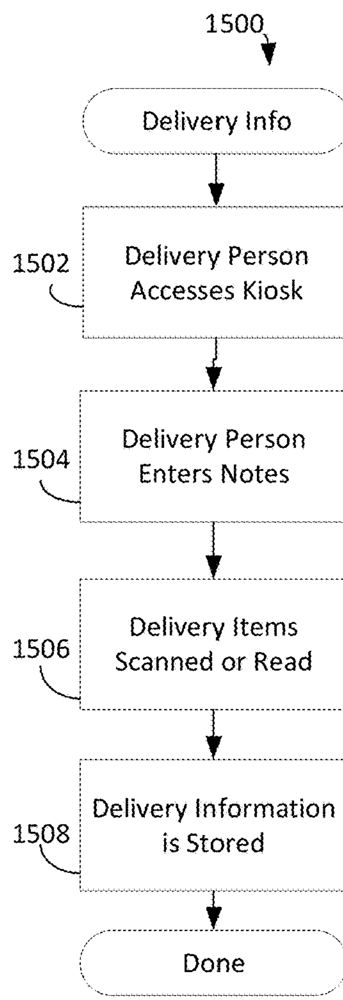

The person transferring may interface with housing via display 106A and 1300 to provide transfer information. The person can be the seller, buyer or third party. Flowchart 1500 of FIG. 15 illustrates some of the steps that may be performed in such an instance. Initially, the person may access the housing 1502. The person may enter a note(s) regarding the transfer, such as what was transferred and the state of the digital asset that was transferred 1504. This information may be entered, such as through the display 106A (FIG. 1A) which can be a touchscreen. The transferred items can be read at 1506. As was mentioned above, several different types of input technology may be used on the delivered items. Therefore, delivery information is then stored in records that may be accessed subsequently 1508.

Figures 16, 17:
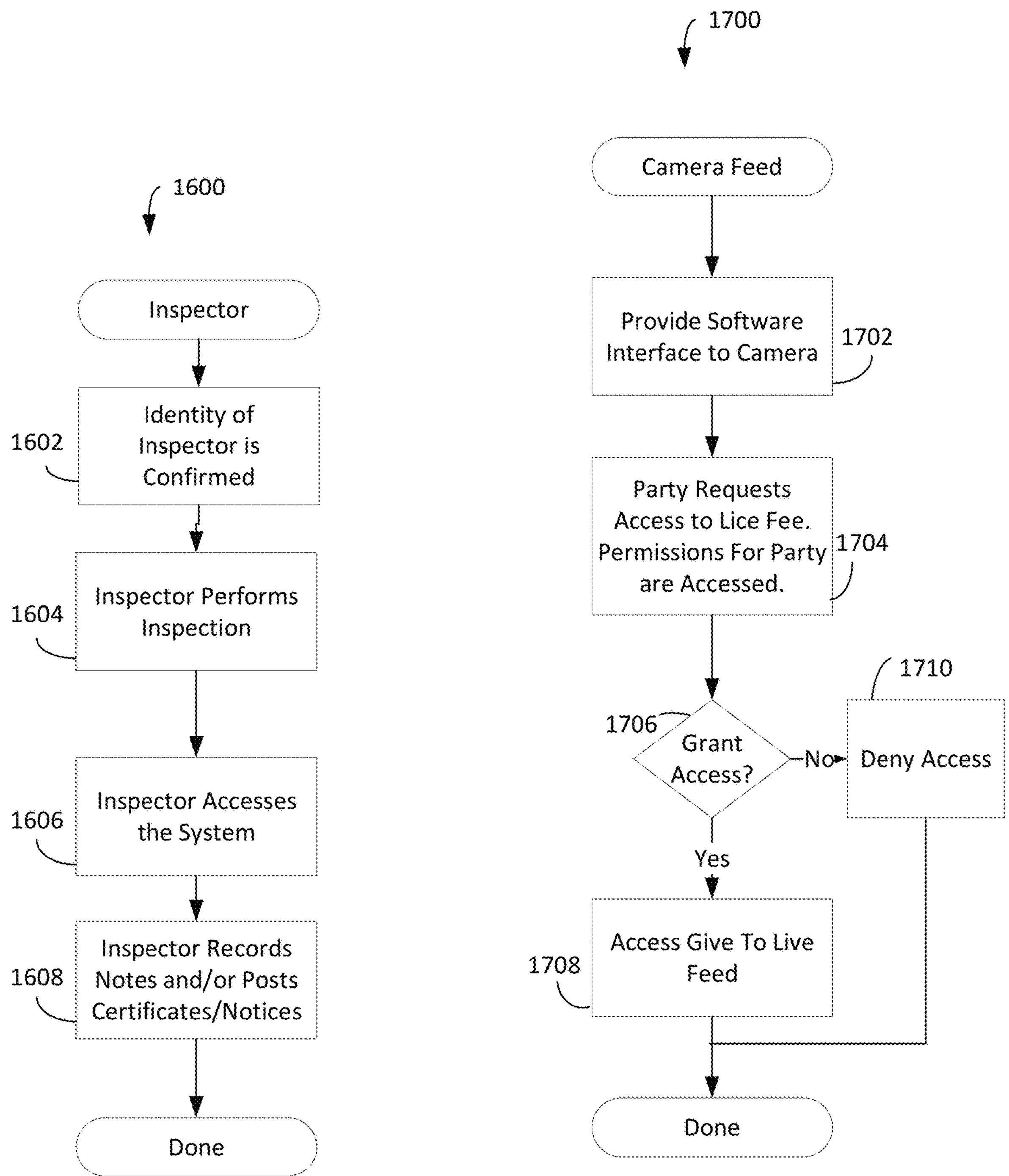

When a transaction, other an original entry of an asset of a subsequent transaction, an individual (e.g., custodian, certifier, inspector, and the like) may interface with the system. FIG. 16 includes a flowchart 1600 illustrating steps that may be performed in such an interaction. Initially, the identity of the inspector may be confirmed using the biometric data 1602 or manually using the touchscreen on the system. The inspector then performs the inspection of the digital asset at the use location 1604. The inspector then accesses the system at 1606 and provide information about the digital asset as well as the system reading information about the asset. The individual then may record notes and/or post certificates, notices, or other information at the system 1608. Additionally, the inspector may use technology available via the system such as OCR scanner, camera, or the like to capture appropriate information the individual may include during the creation, recording or otherwise making of the digital asset or transaction. If the system is at a trade show, for example, the metadata about the transaction can be recorded including the seller, buyer, date, time, location, certification, verification, and the like. In one embodiment, the system can create a certification using the verification methods herein where the metadata associated with the digital representation can serve as verification.

The system may include a still camera(s) or a video camera(s). FIG. 17 provides a flowchart 1700 relating to such access. A software interface to the camera may be provided to enable authorized external parties to gain access to the camera 1702. A party requests access to the camera via the interface over the network 1704. For example, a bank official may wish to view the use location before authorizing release of funds or before granting a loan. A determination is made whether the party is permitted access by accessing permissions 1706. The system gathers a great deal of information over the course of time. At least a portion of this information is persistently stored to compile a record of activities at the use location. This record can be useful to prove activities after the fact. The activities that are recorded may drive workflow and scheduling at the use location to improve efficiency. If the party is permitted access, access is given to the party so that they may create, transact with or transfer a digital asset and review and receive a captured image or video data 1708. Otherwise, access to the camera by the party is denied 1710.

Figures 18, 19:
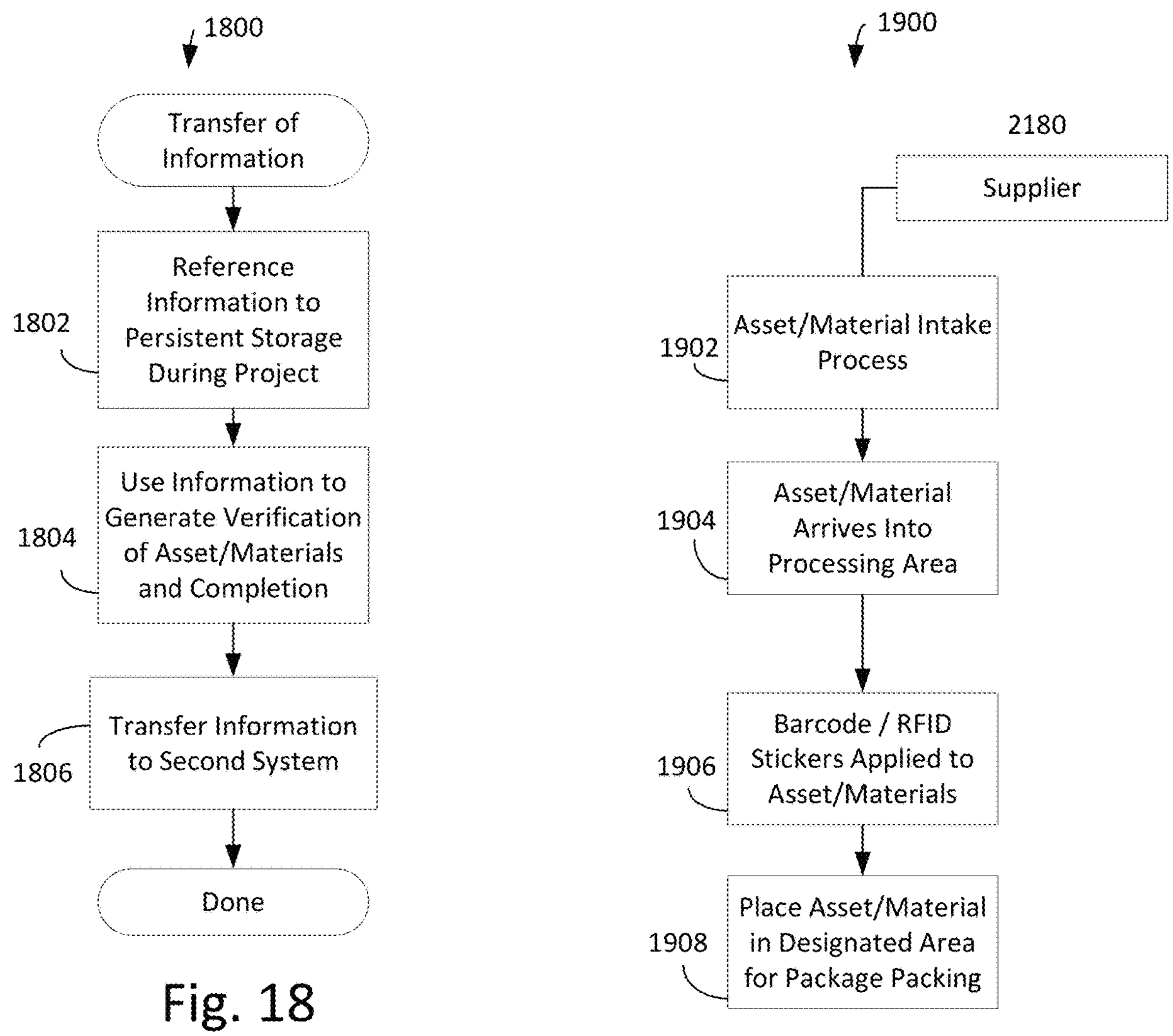

FIG. 18 shows a flowchart of steps 1800 that may be performed in exemplary embodiments in relation to the information. The information obtained about the digital asset can be derived from many different sources may be stored on or referenced from persistent storage 1802. This information may help resolve disputes between parties concerning authentication. Since there is a complete record on the persistent storage of all transaction, individuals, activities, tasks, locations, and the like associated with the digital asset these records may be accessed to resolve the dispute. Insurance providers may access these records referenced on the persistent storage to provide insurance or confirm claims. Inspection records may be accessed to confirm that proper inspections were carried out and passed.

A verification can be created and stored at 1804. A certificate of authenticity can be emulated based upon the digital asset and associated with any subsequent transaction and stored on the persistent storage.

The information referenced in the persistent storage may also be accessed from a computing device of an owner, seller, buyer, inspector, proposed buyer, insurance entity, creditor, customer, and the like at 1806. In exemplary embodiments, information may be gathered from and sent to multiple parties including a managing company responsible for the management and oversight of a digital asset.

The creating company 1910 can be responsible for the intake of content and other materials specified in the material requirement record that are needed for the project or process that results in creation of a digital asset. FIG. 19 shows a diagram 1900 of steps taken in the material intake process 1902.

Figure 20:
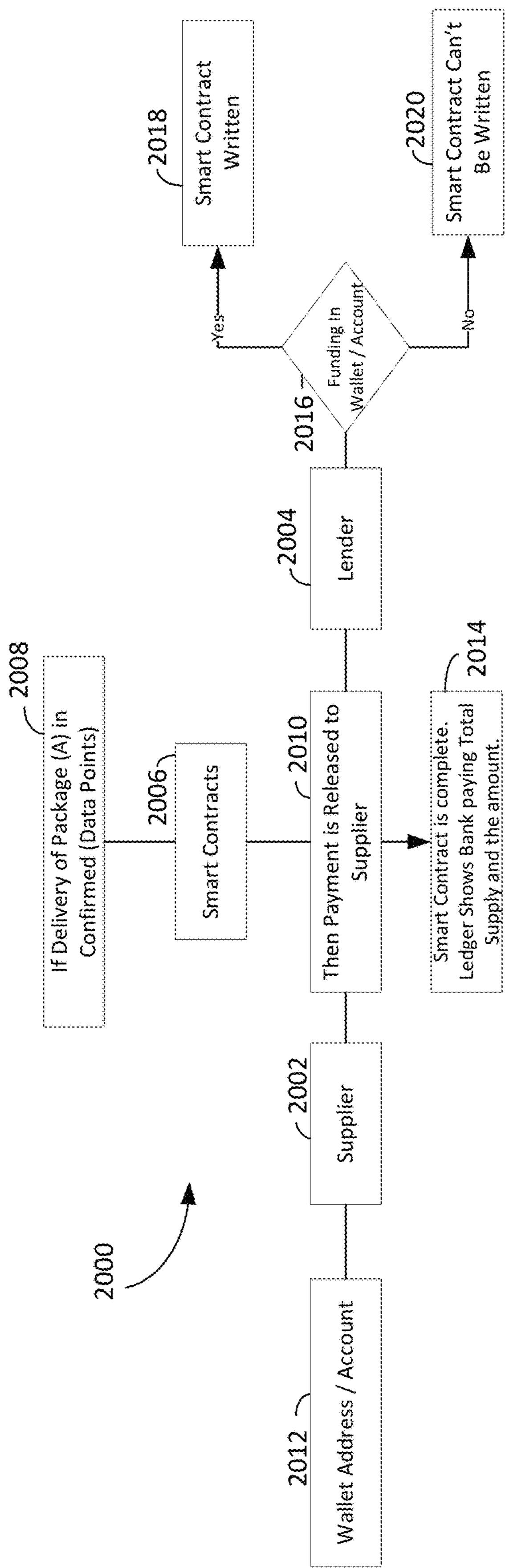
FIG. 20 shows different types of input technology.

FIG. 20 shows a diagram 2000 of a first example of interactions relating to a smart contract for the project or process. Suppose that the supply company 2002 makes a transfer of the digital asset. Further suppose that the transfer is confirmed 2008 by information such as that gathered by the system as discussed above. The buyer (e.g., payor) 2004 can releases payment 2010 to the creating company 2002. Creating companies can include a sports team, league, artist, and the like. Payments can be made through third party funding, factoring, credit lines, loans, or other financial option to assist with financing and cash flow management.

The payment may be made electronically, such as through crypto currencies, like Bitcoin or Ethereum, or via a stable coin whose value is pinned to an item like a paper currency or the like. A cryptocurrency is a digital currency built with cryptographic protocols that make transactions secure and difficult to forge. Other Suitable forms of electronic payment includes Automated Clearing House (ACH) payment, Electronic Funds Transfer (EFT), card payments, other types of bank transfers or other types of electronic wallet transfer. In the case where crypto-currency is used, the crypto-currency may be delivered to the digital wallet of the supply company at a specified wallet address or account 2012. The ledger may be updated to show that the contract is complete 2014. Payment requires that the lender has sufficient funding in their digital wallet 2016. If not, the smart contract will not be written on the persistent storage 2018. If there is sufficient funding, payment is made, and the contract is written onto the persistence storage as complete at 2020.

To verify the creation of a digital asset, the system can capture individuals and events at various points during the creation of the digital asset. Pairing these verifications with the virtual representation can include several elements or components. Included in the pairing process can be the physical observation of a physical material and then associate the physical material with the digital asset so that the physical material is properly associated with the virtual representation. This verification provides truth that the virtual representation is accurately associated with the physical material or actual event as a factor rather than simply trusting that the virtual representation is accurate. This system can use manual or automated processes to physically observe the material and event and associate the digital asset during various events from creation to raw material to final digital asset. Verification can also use the metadata that is associated with the interaction of physical items by individuals and electronics when the digital asset is created, displayed, transferred, activated, and destroyed. The metadata that can be captured and placed into immutable storage can provide stakeholders an audit trail of history for their physical asset using a verified paired virtual representation. A similar process as described herein can be used for pairing a biometric identifier with an individual.

By verifying the digital asset, the risk of unintentional or impermissible rehypothecation can be reduced or eliminated. The digital asset can be verified by multiparty chronological metadata streams that can be associated with a physical location. Because verifications using these streams are chronological, altering the information could require alteration of the metadata prior to and after the altered record. Therefore, the altered record would be inconsistent with the associated records potentially both temporally and geographically and an attempt to alter the record would be discovered. The use of a persistent storage further reduces the risk of alterations of records as well as increasing the verification of information. Further, creating digital assets associated with the event, involving the asset, interactions with the asset and the associated metadata provide for a substantiated digital asset, reduce, or eliminate risk and improve capital efficiency. Further, the pairing of assets facilitates commerce by allowing electronic transactions with assurances that the virtual representation used in the electronic transaction is paired with the physical asset.

Verification, including verification of an event, can include verifying that the physical material and the virtual representation match and can be accomplished in a variation of methods including interaction with identification elements such as a tag, label, and the like, capturing an image of the material, capturing a video of the material, capturing a tag physically affixed or otherwise associated with the material, human visual inspection, and any combination. Identification of an individual performing or otherwise associated with an event can be captured by identification devices (e.g., cards, tags, scanners, RF ID) and biometrics including visual capture (e.g., facial recognition), voice recognition, iris scan, fingerprint, palm print and any combination.

Figure 21A:
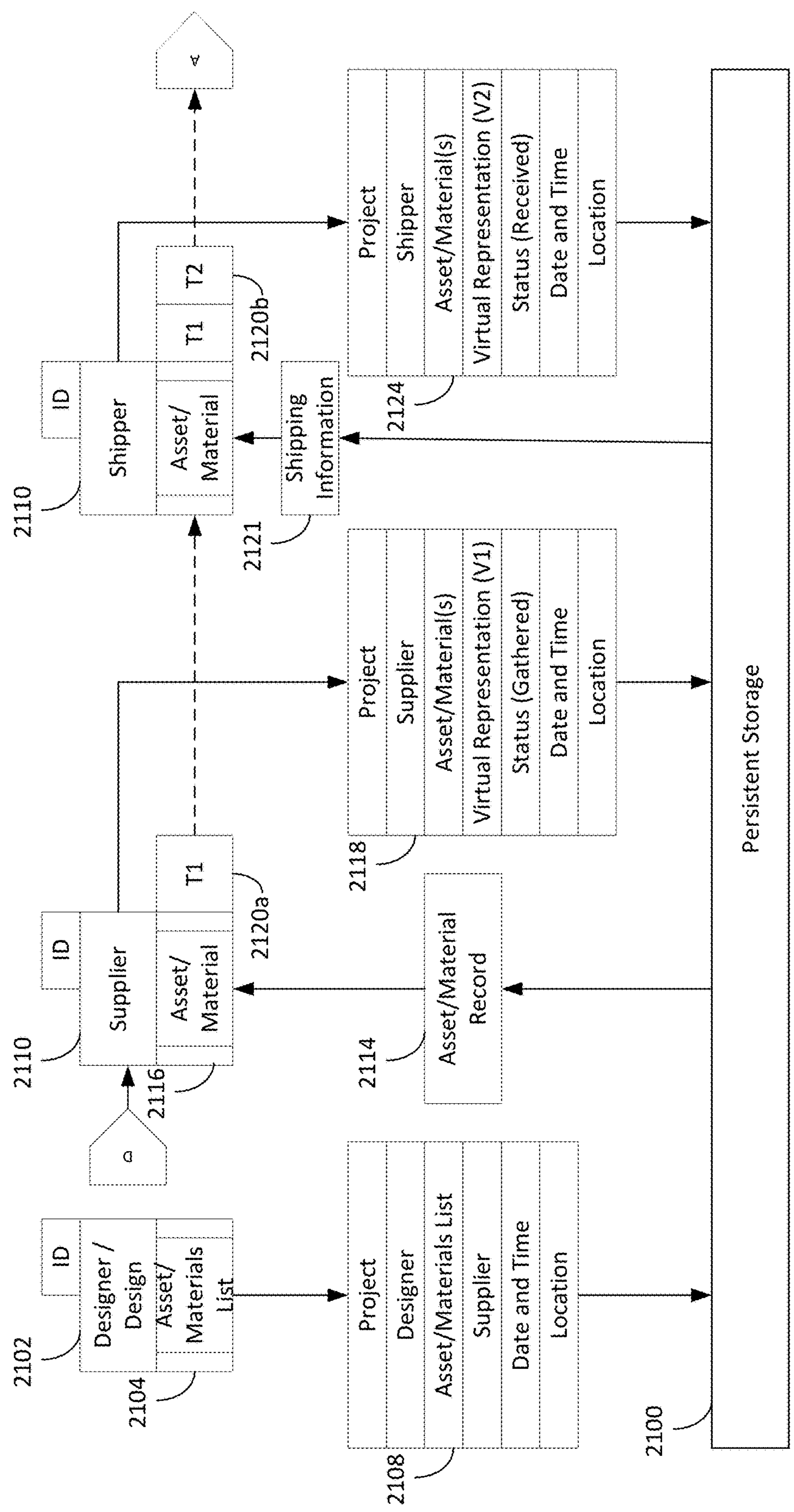
FIGS. 21A-21E shows schematics of aspects of the system.

Referring to FIG. 21A, an exemplary embodiment is shown where the digital asset can represent a physical object rather than when the digital asset is the asset itself. The persistent storage 2100 is accessible by a designer using a designer computer system 2102. The designer can have a unique ID associated with it. The designer can create a physical object such as shape, part, graphic, project, process, or other item or activity. Therefor the digital asset can be an image of the physical object such as a collectible sports card (e.g., baseball card), sporting equipment, (e.g., baseball) and can be for general use or specific use (e.g., the World Series). The design can include a material list and other properties for the object. The system can create a designer record 2108 that can include information associated with the digital asset, its creation, supplier, use location, the date and time the design was created or modified and the location where the design was created or modified and other metadata. The design record can be stored on the persistent storage that can be local or remote from the designer. On one embodiment, when the digital asset is the asset itself, the design record can include the components of the digital design such as space, texture, values, patterns, forms color, lines, contrast, balance, unity, movements, shape, capture angle (e.g., camera placement), scanning rates, and others and any combination thereof.

From the design record, a material record can be created and stored on the persistent storage. The material record can include a single component or multiple components. For example, the material record can include the components of a digital image, a logo, and other items to be included in the digital asset as well as materials used in the paired object.

A creator (supplier), using a supplier computer system 2110, can select or otherwise acquire necessary material 2116 identified on the material list from a materials record 2112 or designer record that can be retrieved or otherwise received by the supplier computer system from the persistent storage. The supplier can verify that the material matches the material requirement record, and the system can capture this event. For example, one method of associating the physical material with a digital asset is using a tag 2120*a* ($T_1$) placed on the material. The tag is then physically verified to be associated with the material from the material list or the material record. In one embodiment, the tag can be electronic can be added to the digital asset or the digital asset record directly such as with adding a hash. Therefore, the physical material and the virtual representation ($V_1$) are paired by recording this event and associating the physical material, $T_1$, and $V_1$. The material can be received by the manufacturer, scanned or otherwise identified with a sensor assembly, inspected by an individual and the manufacturing process recorded. This can include capturing the metadata associated with the material, individual, locations, date, time, and process as stated herein. In one embodiment, the tag can include the following information:

| Description | Digits | Information |
|---|---|---|
| Locations | 19-20 | GPS XX.XXXXXX XXX.XXXXXX |
| User ID | 8 | SSN XXXX + Initials XX + Gender X |
| Date | 10 | XX/XX/XXXX |
| Time | 7 | Zulu XXXX:XX |
| Material | 12 | UPC/Barcode XXXXXXXXXXXX |

A supplier record 2118 can be created and stored on the persistent storage. The capture event can include a unique number and include the supplier ID, date and time, location, material ID, status, and any combination. The material ID can be from an original manufacturer, an entity in the supply chain, value added supper, or other supplier or a creator in the case of a purely digital asset. The status can include that the material has been gathered, manufactured, packaged, ordered, is in stock or on back order, shipping information and any combination. The supplier record can include or reference a designer or manufacturing specification record that can include the material and design requirements. The shipping information can include the origin, destination, shipping instructions, shipper, and any combination and can be included in or reference to the supplier record.

Figure 21B:
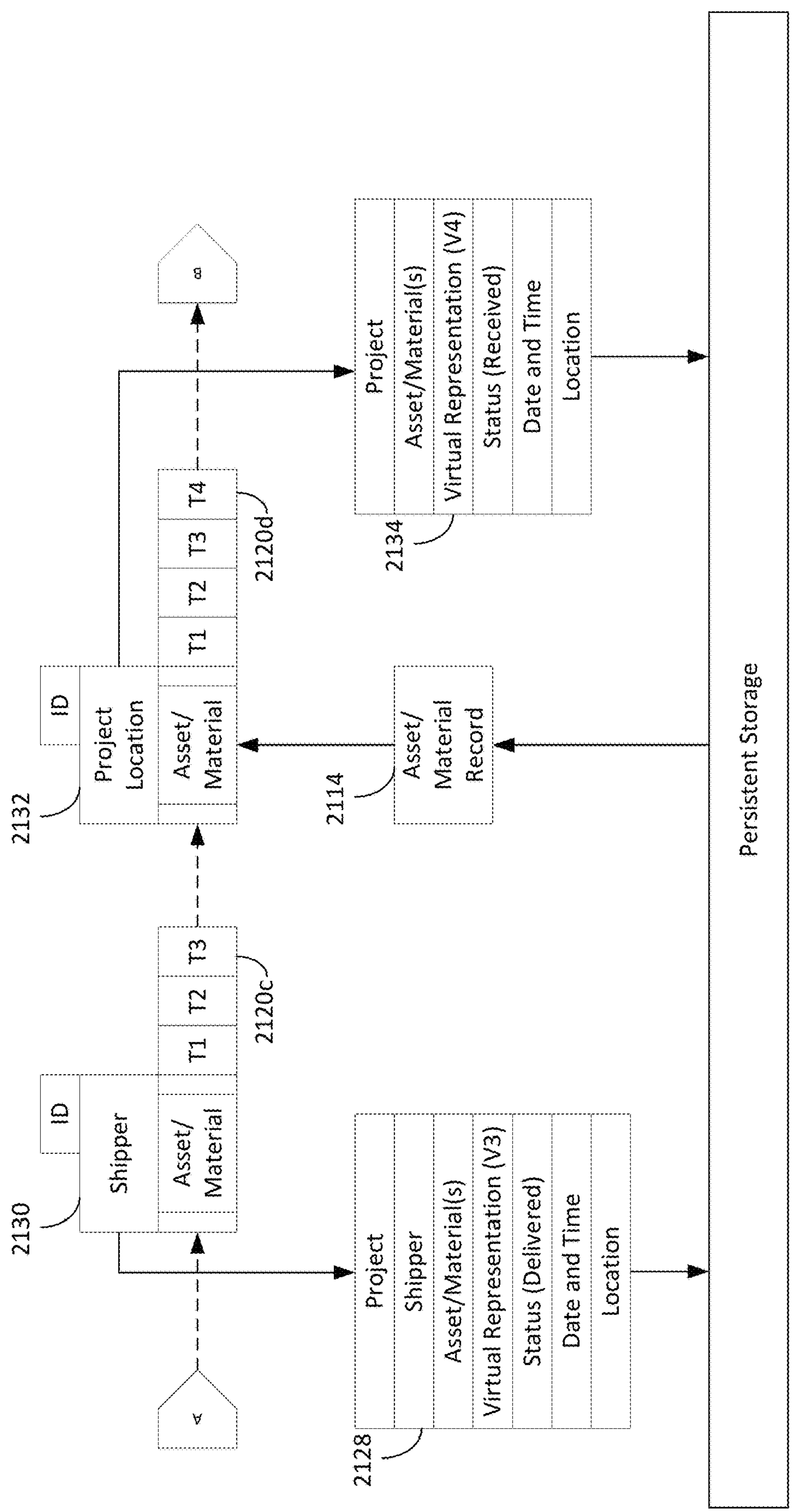

In the event that digital asset is paired with a physical object or event, and referring to FIG. 21B, a shipper can retrieve shipping information from the persistent storage 2122 identifying the material or asset location, transfer, load, destination, pick time, delivery time, and other information concerning the shipping of the material or asset. The shipper can verify that the physical material or asset being retrieved from the supplier match the virtual representation of the supplier record. If the materials are verified, the shipper can physically capture the event, for example, by affixing its tag 2120*b* ($T_2$) to the materials representing this verification. A supplier shipping pickup record 2124 can be created and stored on the persistent storage. The supplier shipping pickup record can include project, shipper, material, status, date, time, location, and any combination. The mode of transportation of the material can also be tracked and stored on the persistent storage. For example, if the shipper uses a vehicle, the date, time, location, and other metadata associated with the vehicle can be gathered along the route and stored on the persistent storage. If the shipper uses a certain computer device or system of digital capture equipment, the date, time, location, and other metadata associated with the system of equipment can be gathered.

Verification can be provided using the metadata of the various events associated with the material or asset. For example, if the date, time, and location of the supplier record is within a certain range of values of the date, time and location of the supplier shipping pickup record, there will be verification that the proper materials were physically transmitted from the supplier to the shipper. In the event that the digital asset is the asset itself, verification of the digital asset can be provided using the metadata of the various events associated with the creation or transaction associated with the digital asset. For example, the date, time, and location of the creation can be within a certain range of values of the date, time and location of the creator, there will be verification that the digital asset was created by that creator.

Figure 21C:
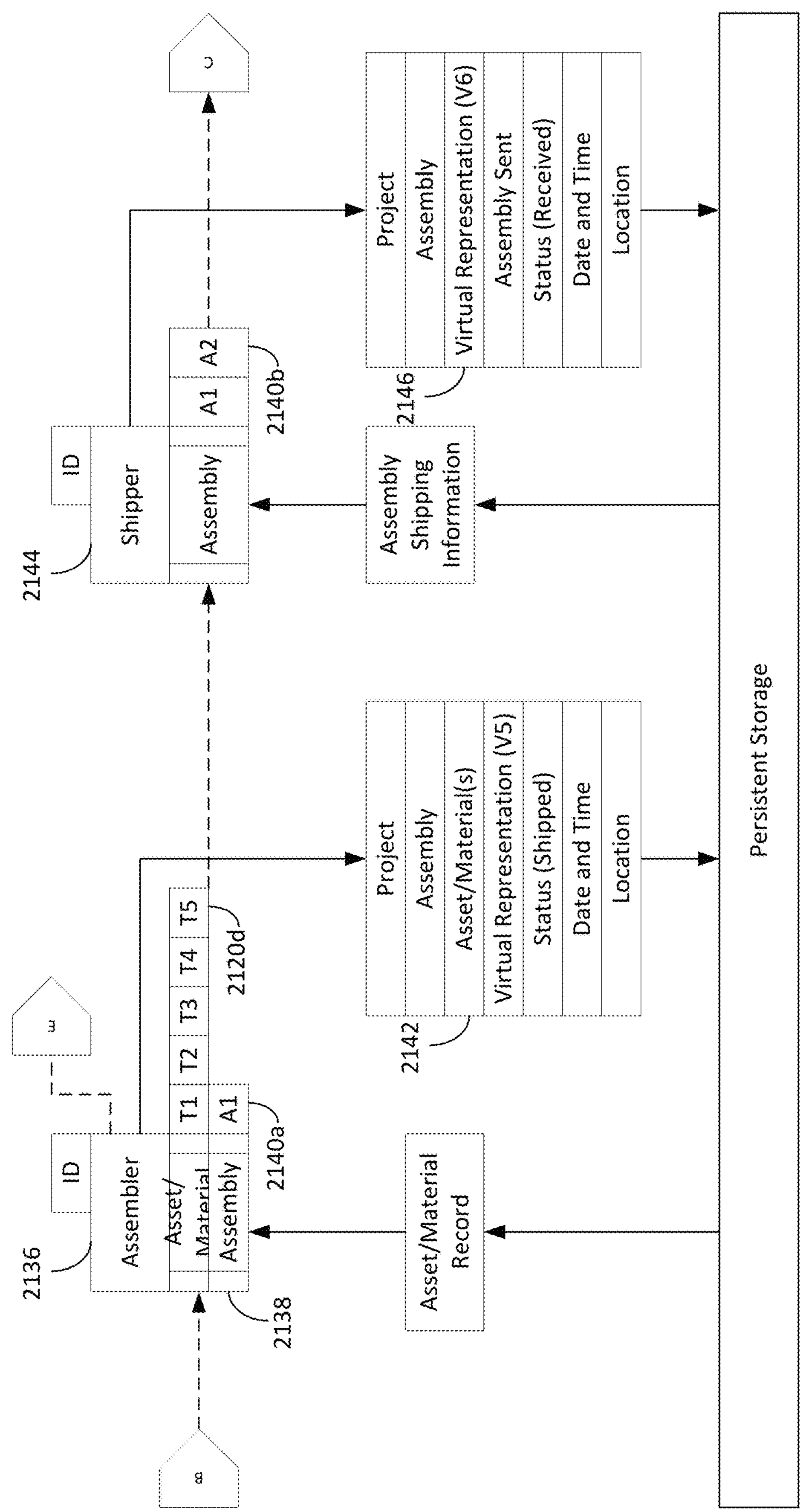

Referring to FIG. 21C, the use location can be a location that can create or transfer the digital asset, add significance to the digital asset (e.g., a baseball, bat, glove, jersey, or other articles used for a record such as during a xxth homerun or have it signed), authenticate the digital asset (or associated physical asset), or other activity. For example, if a baseball is used for a xxth homerun, an individual with authority at the use location (e.g., stadium) can verify the baseball, add a unique identifier, record a pre-existing identifier, capture an image of physical asset, have it signed, and any combination and add the information into the system. The use location can be the location where the digital asset is created, such as the location of a camera when an image or video is created. The system can verify the information using the sensor assembly including capturing information about the digital asset, individual, event, capture equipment, creator, and the like. If a unique identifier is used, it can include a number, bar code, alpha numeric characters, QR code, RFID, beacon, lot, size, sticker, tag, hologram, label, wireless transmitter, wireless transceiver, physical feature, and any combination. The physical feature when the digital asset represents a physical object can include a surface structure on a physical asset, a microstructure or other characteristics or manufacturing characteristics such as tool marks. The unique identifier can include material identification added or associated with the digital asset record.

The system 2136 can be used to retrieve the digital asset record from the persistent storage. The digital asset record can be used to match the digital asset create or verified at the use location to verify that the digital asset is properly associated with corresponding significance (e.g., the xxth homerun, at the corresponding date, time, event, location, and the like). The use location can add tag 2120*d* ($T_5$) to the digital asset, or use other verification methods described herein, to capture the event and the digital asset. The system can also capture the digital asset and corresponding event or significance at 2138 by adding a tag 2140*a* ($A_1$) to the digital asset. A digital asset record 2142 can be created, modified, stored or any combination on the persistent storage. The record can include the event, location, description, virtual representation, date, time, location, other metadata, and any combination.

Once completed, the digital asset can be transferred to another location such as through a transmission, sale, or loan. The digital asset record can include shipping information, or a digital asset transfer record can be created and stored on the persistent storage. If the digital asset needs to be transferred (electronically or on electronic media), a second shipper can use a second shipper computer system 2144 to retrieve the shipping record, digital asset record or other shipping information that is used to identify the origin, locations, digital asset, pick up time, delivery time and other information associated with the transfer of the digital asset from one location to another and from one owner to another. The digital asset can be received by the second shipper and the second shipper can capture the event such as with a tag 2140*b* ($A_2$) to the digital asset record representing that the digital asset has been verified by the second shipper as properly provided and received by the shipper. A second shipper pick up record 2146 can be created and stored on the persistent storage.

Figure 21D:
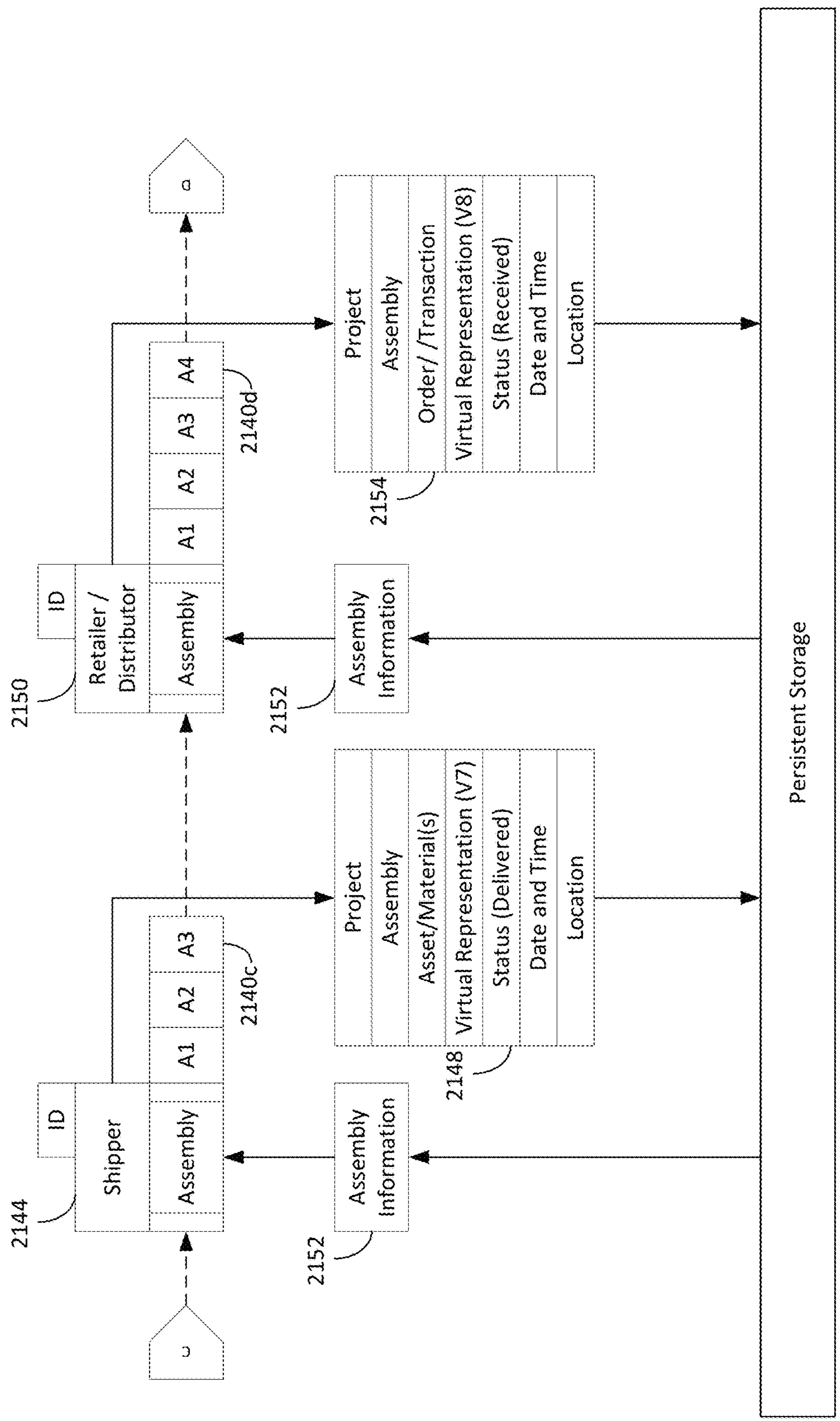

Referring to FIG. 21D, the second shipper can transfer the digital asset to a retailer, distributor, or customer. The digital asset can be transferred from an original owner to a subsequent owner. When the second shipper transfers the digital asset to a retailer or distributor, the second shipper can create a second shipper delivery record 2148 using a second shipper computer system 2144. The second shipper can capture the event such as using a tag 2140*c* ($A_3$) representing that the proper digital asset was delivered to the proper location. The second shipper can use the verifications that are part of the virtual representation to match $A_3$ with the digital asset and the information stored on the persistent storage.

The retailer or distributor computer system 2150 can be used to verify that the digital asset is properly transferred by retrieving the digital asset record 2152 or second shipper record 2148 from the persistent storage and using the record to match the physical asset delivered. The retailer or distributor can capture the event and can add a tag 2140*d* ($A_4$) representing that the proper asset was received at the proper location. A retailer distributor record 2154 can be created and stored on the persistent storage. Therefore, when a subsequent entity wants to verify the digital asset authenticity, the persistent storage includes the audit trail and chain of custody for the digital asset. Significance of a digital asset can be any occurrence, event, individual or other circumstances which differentiates the digital asset from other assets. For example, an image of a baseball that is used during a World Series game has increased significance from one used by a team at a practice. The significance can increase the value of the digital asset.

A baseball league may originally have ownership of the digital asset and therefore the right to transfer the digital asset to a second entity. The transaction can be recorded that can include the device ID of the kiosk, tag information of a tag associate with the digital or physical asset, exchangeable image file data or other data associated with a photo of the physical asset, biometrics of the certifier, seller, buyer or other individual associated with the digital asset, location and time certifications of certifier, buyer, and seller, wallet confirmation, digital asset number, hash confirmation, audit information, location over time for the digital asset and other information described herein. The system can also store digital assets and transactions associated with the buyer and seller and generate transaction history for the buyer and seller, jointly or separately that can include the data described herein.

Figure 21E:
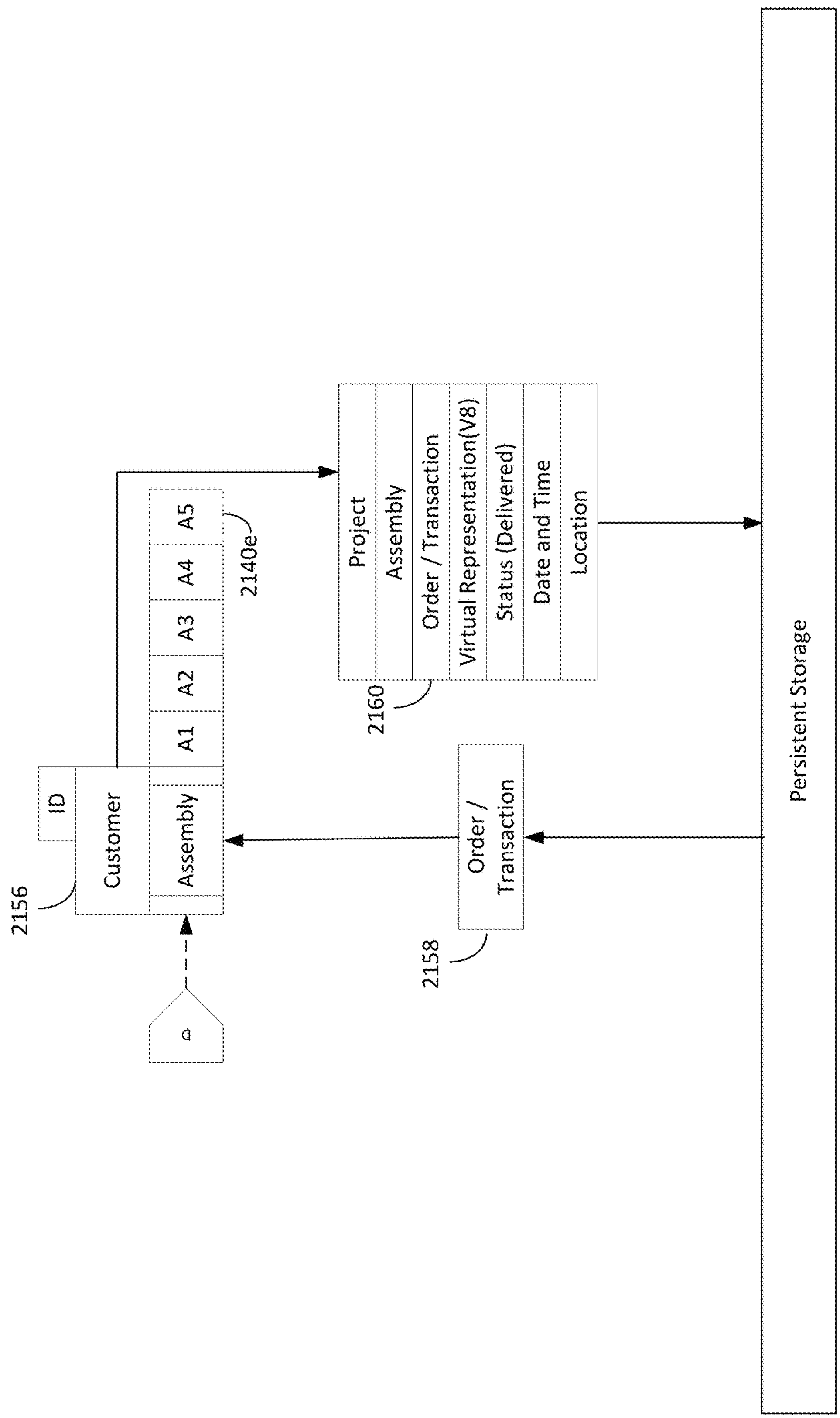

Referring to FIG. 21E, a buyer can receive the digital asset as using a computer system 2156 to retrieve or otherwise receive an order record 2158 from the persistent storage or other system requesting that a customer receive the digital asset. The system can be located at a trade show or other location where a transaction can occur. The buyer or recipient of the digital asset can receive the digital asset using the system as described herein with a shipper performing the steps and the system performing the steps associated with the shipper and second shipper above. The buyer can receive the asset physically at a second location such as a trade show. A third shipper can create a third shipper pickup and delivery record that can be stored on the persistent storage verifying that the digital asset was properly provided from the owner or distributer to the customer or buyer. The customer may capture the event and can add a tag 2140*e* ($A_5$) to the digital asset that can be associated with the virtual representation ($V_8$). A customer record 2160 can be stored on the persistent storage.

Using this system, the buyer or other entity can be assured that the digital asset was independently verified and authenticated from the original creation, from the manufacturer to delivery at the venue or event location, the anchored location the immutable time verification biometrics of officials and or event participants and pictures or other unique identifiers of the object itself at the event. Original owner or certifying entity, for example a sports league. Therefore, when a buyer purchases a digital asset, such as collectibles or memorabilia, the authenticity can be quickly and easily verified at the location of purchase (e.g., trade show) by accessing the persistent storage without the need for a third party or professional authentication process.

The system described herein can pair the physical material (e.g., physical asset) with a virtual representation where the virtual representation can be the digital asset or can be represented by the digital asset. Failure to pair a physical asset with the virtual representation can negatively impact areas such as authentication, certification, verifications, fraud prevention, and the like. Tracking, management, and verification of materials and assets to ensure authenticity and use and manufacturing is an important aspect to many assets and their valuation. Tracking and record keeping during the life of an asset from its creation to use can be difficult to perform without the ability to pair the asset with a virtual representation.

Systems at multiple locations may be interconnected using image capture devices, RFID, QR codes, barcodes, biometric scanners, still cameras, video cameras, and the like to identify individuals or machines that are performing verifications during the process. Further, multiple individuals or machines are performing verifications so that there is not a reliance upon any one entity for verifications. The processing of capturing data, including images, from the multiple systems at multiple locations can be used to improve the verification of proper materials and assets as well as to pair the physical items with the virtual representation.

This process can include internal and external individuals and machines for performing inspections (e.g., verifications) . For example, the system can receive a set of internal inspection information entered into the system from an internal inspector representing an internal physical inspection of the project, material or assembly. As the items travel, an internal inspector can provide inspection information representing the stages of the project. The system can also receive a set of external inspection information from an external inspector and an external inspection computer device representing a third-party physical inspection of the project at predetermined stages of the project. Based upon the internal inspection, external inspection or both, an inspection record can be created and stored on the persistent storage.

Figure 22:
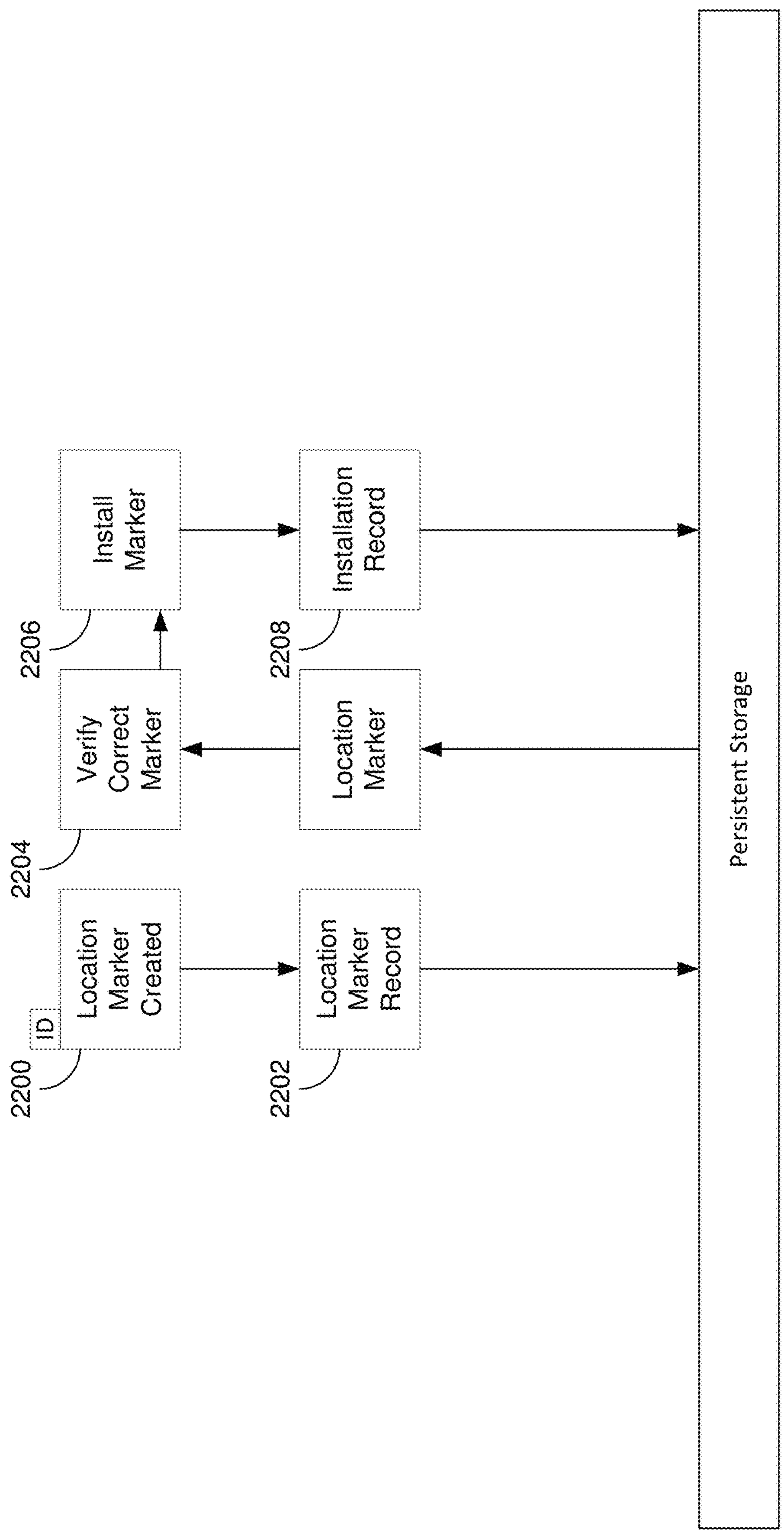
FIG. 22 shows schematics of aspects of the system.

Referring to FIG. 22, a location marker 2200 used to uniquely identify a location such as a use location and can include a stadium, playing field, trade show, retail location, distributor, wholesale location, warehouse, asset location, or other physical location. The location marker can be a barcode, RF ID, placard, sign, plaque, QR code, or other symbolic, alphanumeric, digital, or electronic identifier. When creating the location marker, a location marker record 2202 can be created that includes the location marker identification information, creation date, maker, manufacturing location and other information that can be stored on the persistent storage. The installed information can retrieve the location marker record and match the retrieved information with the physical location marker to verify that the correct location marker is being installed at 2204. The installed can physically install the location marker and using a GPS enabled device, read the location marker, and create a location marker installation record 2208. The installation can be paired with the physical location marker and/or the physical location of the project. The metadata from the GPS enabled device can be included in a location marker installation record that can also include installer information, date, time, location marker information and physical location information and can be stored on the persistent storage. Therefore, the physical location marker is verified to be paired with the use location and a virtual representation of the location market and use location.

The system can be used to confirm a creator and design specifications from the creator. The creation and creator may have a unique identification. IF the digital asset if associated with a specific object, the object can be confirmation and included in the digital asset record to verify the location and time of creation or other event and transaction. Within a predetermined period of time of arrival at a use location, an object can be used with or at an event (e.g., a sporting event) whereby, for example, the visiting team pitcher would use a baseball and pitch to a home team notable player, the notable player could then hit a homerun into the home team bullpen. The baseball would easily be retrieved by stadium or other personnel associated with the use location, team, league, and the like. The baseball could then be taken to the computing device where the official could creation a digital asset and associate the digital asset with the object and register it at computer device and kiosk. The kiosk can confirm the location, and the time of registration by immutably recording the baseball into a digital asset record. The biometrics of the official would then be recorded into the same record. The kiosk can also be used for verification of the digital asset itself, such as a digital image, video, digital art and the like. When the digital asset is digital art, the digital art can include attributes such as duplicability, interactivity, networkability, variability and compositeness.

Duplicability is whether digital asset, such as digital art, was created from a pre-existing source such as the litigation of a physical object or whether the digital art originated digitally. For example, a digital image of the Mona Lisa would be the digitization of a pre-existing work and a conversion from analog to digital. A work such as computer-generated imagery is an example of digital art with a digital origin. Interactivity is the ability of the viewer to engage with the digital art including the ability to walk in, on or around the digital art or otherwise interact with the digital art. The digital art can react to input through sensors that can detect motion, temperature, meteorological changes, proximity, and other types of input. Networkability is the ability of the digital art to be networked with other digital items include other computer systems, displays, networks and the like. Variability of digital art is when the installation of the digital art is constantly in flux and for which identity was constituted by each instantiation of the artwork at any given time of its lifespan. For example, if the digital art is immersive such as broadcast on the interior walls of a room, when the digital art is moved from room to room the display of the images on the interior walls changes with the configuration of the room. Compositeness of digital art is the structure of the visual aspects of the digital art. It includes the relations between the components of the digital art such as the negative and positive space and each component the creator (artist) chooses to include in the digital art and express to the audience.

A digital wallet could hold this digital asset that would give the owner anonymity but proving their ownership. In the future if this owner wished to sell the digital asset a new buyer could evaluate the digital asset in question for purchase by confirming the authenticity of the digital asset. The digital asset can also be verified to be associated with a sporting event where the memorabilia or object was used if the digital asset represents a physical object. The digital asset can be authenticated with their digital wallet to confirm that their digital wallet contains the digital asset record and agreed to price between the parties could be entered into a smart contract tied to transfer information whereby the digital asset can be transferred to the new buyer and upon confirm transferred by a third party and confirm the time of purchase or transfer of the digital asset through their personal computing device or by going to a location with a computer device and kiosk.

In one embodiment, wallet addresses can be used to improve security and authentication by limiting the number of authorized wallets for a given object, digital representation, owner, transactions or the like. Further, funds could be placed in an escrow account whereby upon confirm delivery the funds are transferred to the original owner or initial owner and the digital asset is transferred from the original owner's wallet to the new owner's wallet making their wallet the new owner of record. As the digital asset database is immutable a historical or chronological record of all wallets that the digital asset had been in would be kept proving additional provenance on the item for future buyers the digital asset database could be referenced or endorsed by the major-league baseball league and each time a sale was to occur a fee, commission, could be paid to major-league baseball, the players, or other identified relevant parties. The new owner can have the digital asset, an as applicable, physical asset transferred in this matter to provide verifiable provenance of the item in continuum for future value confirmations, sales, or other transactions.

If the digital asset represents a physical asset and the owner want to take the object to a tradeshow for sale. A computer device could be present to record location, time, and biometric confirmation from seller to buyer as well as to scan the object itself and confirm that the unique identifier matches the original asset such as by using a tag. At a tradeshow the owner of the object can physically take the baseball to the computer device (e.g., kiosk) authenticated through the scanning of the affixed identifier, confirming the party's identity through biometric scan and confirm the location of the event where transaction occurs including the time of the transaction. The buyer could enter wallet information, confirm their biometrics, and effectuate the value transfer through smart contract or in person payment. Upon confirmation of payment by the seller the digital paired digital asset would be transferred to their wallet and the kiosk could confirm. Pairing the actual sale transaction in this way would give further assurance that the item is the object paired with the digital asset immutable database.

One of the most forged items is memorabilia or items that have been signed by an athlete, performer, politician, or other. It is often impossible to authenticate signatures as some signatures can be easily copied. In the case of using the system to digitally paired memorabilia an athlete could sign these items at a tradeshow and use the kiosk at the key tradeshow to authenticate or digitally pair the items using their biometrics, the location anchoring, the time, and pictures through the kiosk of the item. Each asset (physical and digital) can be given a unique digital asset number which future purchasers could confirm the digital asset number relative to the item being bought, sold, or traded it would be of great advantage for athletes and others to digitally pair all memorabilia and other items that they sign to the system to ensure authenticity. This can increase the market value of items as well as reduce or prevent fraud. If should be noted that the digital asset can be authenticated in one embodiment without the need for inspection of the physical asset if the digital asset if the item being transferred without necessarily physically moving the physical asset. For example, if the digital asset represents artwork, the ownership of the artwork can be transferred by digital asset transfer without necessarily moving the artwork, for example, if the artwork were displayed in gallery.

What is claimed is:

1. A computerized system for a creation and management of a digital asset comprising:

a computer system disposed at a use location and in communication with a persistent storage;

a sensor in communications with the computer system;

a set of non-transitory computer readable instructions included in the computer system adapted for:

receiving a digital asset from a creator of the digital asset;

receiving identification information using the sensor of the creator;

retrieving location information representing a physical location where the identification information is received, the digital asset is received, and the computer system is located when the digital asset is received;

retrieving a date and time information from the computer system;

creating a digital asset record that includes a unique identifier associated with the digital asset, identification information, location information, and date and time information; and, storing the digital asset record on the persistent storage.

2. The computerized system of claim 1 wherein the set of non-transitory computer readable instructions are adapted for receiving an origination information taken from a group consisting of date, time, event, individual, team, organization, notation, and any combination thereof.

3. The system of claim 2 wherein the origination information includes information of a first individual confirming the origination information and associating the origination information with the asset.

4. The system of claim 2 wherein the origination information includes a raw material information representing a raw material used to make a physical asset associated with the digital asset and a manufacturing verification information representing that a manufacturer physically verified that the material used in the physical asset is the same material used in a design associated with the physical asset.

5. The system of claim 2 wherein the origination information includes a manufacturing information associated with a physical asset represented by the digital asset.

6. The computerized system of claim 1 wherein the identification information is a biometric information.

7. The computerized system of claim 6 wherein the biometric information is taken from the group consisting of facial recognition, voice recognition, retinal scans, fingerprint scanners, hand scanners and any combination thereof.

8. The computer system of claim 1 wherein the digital asset is an immutable digital asset.

9. The computer system of claim 6 wherein the digital asset is an immutable digital asset at its creation.

10. The system of claim 1 wherein a use location is included in the digital asset record and is taken from the group consisting of a sporting stadium, physical asset manufacturing facility, distribution facility, sales location, gallery, studio, IP address, digital asset creation location, event, gathering, assembly, and any combination thereof.

11. The system of claim 1 wherein the digital asset record includes an attribute record information representing the attributes included in the digital asset.

12. The system of claim 11 wherein the attributes are taken from a group consisting of duplicability, interactivity, networkability, variability and compositeness.

13. The system of claim 1 wherein the digital asset record includes biometric information of an individual associated with the digital asset.

14. The system of claim 1 wherein the digital asset record includes biometric information of an individual at an event associated with the digital asset.

15. The system of claim 1 wherein the location information includes an event information taken from the group consisting of a sporting event, political event, entertainment event, transaction event, signature, autograph, nostalgic event, and any combination thereof.

16. The system of claim 1 wherein the digital asset record includes biometric information of an individual during a transaction associated with the digital asset.

17. The system of claim 1 wherein the digital asset record includes information associated with a creation of the digital asset.

18. The system of claim 1 wherein the set of non-transitory computer readable instruction are adapted to retrieve the digital asset record, receive a buyer information, receive a seller information, associate the digital asset with a transaction according to the buyer information and the seller information, create a transaction record according to the transaction, digital asset record and a transaction verification information.

19. The system of claim 18 wherein the transaction verification information is taken from the group consisting of a biometric information of the buyer, biometric information of the seller, buyer identification, verification of the seller, verification of the asset and any combination.

20. The system of claim 18 wherein verification of the asset includes capturing an image taken of the asset at a transaction location, transaction date, transaction time, transaction event, buyer, seller of any combination thereof.

21. The system of claim 20 wherein the transaction location includes a location marker associated with the location; and, the computer system is uniquely paired with the transaction location using the location marker.

22. The computerized system of claim 1 wherein the set of computer readable instructions can be adapted to creating a buyer record representing the buyer of the asset and storing the buyer record on the persistence storage.

23. A computerized system for a creation and management of a digital asset comprising:

a computer system disposed at a use location and in communications with a persistent storage;

a sensor in communications with the computer system;

a set of non-transitory computer readable instructions included in the computer system adapted for:

creating a digital asset record using the sensor representing a physical asset associated with a digital asset wherein the digital asset is included in the digital asset record and includes physical asset information taken from the group consisting of date, time, event, team, individual, notation, and any combination, creating a significance record using the sensor having significance information taken from the group consisting of location, date, time, event, team, individual, notation, and any combination, associating the significant record with the digital asset record, and storing the digital asset record on the persistence storage.

24. The system of claim 23 wherein the digital asset record and the associated significance record are configured to be retrieved from the persistence storage from a third-party computer system and adapted to verify that the physical asset is authentic according to the asset record and the associated significance record.

25. The computerized system of claim 24 wherein the computer system is contained in a device taken from the group consisting of a kiosk, tables, laptop, portable device, smart phone, and any combination.

26. A computerized system for a creation, and management of a digital asset comprising:

a computer system disposed at a use location and in communication with a persistent storage;

a sensor assembly in communications with the computer system;

a digital asset having a unique identifier;

a set of non-transitory computer readable instructions included in the computer system adapted for:

creating a digital asset record according to the digital asset adapted to be identified by the computer system, storing the digital asset record on the persistence storage, creating a transaction record representing a transfer of the digital asset from a first entity to a second entity wherein the transaction record includes a transaction verification wherein the transaction verification includes seller biometric information, seller biometric information, date, time and location associated with eh transaction, transmitting a payment request according to the transaction verification to a second entity account representing payment for the digital asset from the second entity to the first entity, and, storing the transaction record on the persistence storage.

27. The system of claim 26 wherein the first entity is an originating entity, and the second entity is a buyer.

28. The computerized system of claim 26 wherein the digital asset record is created according to an origination information representing physical verification of the location of a physical asset associated with the digital asset.

29. The computerized system of claim 26 wherein the digital asset is digital art.

30. The computerized system of claim 26 wherein the digital asset is a virtual representation of a physical object wherein the virtual representation is associated with a physical object.

* * * * *